US007179630B2

(12) United States Patent
Lassen et al.

(10) Patent No.: US 7,179,630 B2
(45) Date of Patent: Feb. 20, 2007

(54) THERMOSTABLE PROTEASES

(75) Inventors: Soeren Flensted Lassen, Farum (DK); Carsten Sjoeholm, Alleroed (DK); Peter Rahbek Oestergaard, Virum (DK); Carsten Andersen, Vaerloese (DK); Morten Fischer, Vedbaek (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/873,593

(22) Filed: Jun. 21, 2004

(65) Prior Publication Data
US 2005/0058747 A1 Mar. 17, 2005

Related U.S. Application Data

(60) Provisional application No. 60/549,761, filed on Mar. 2, 2004, provisional application No. 60/549,349, filed on Mar. 2, 2004, provisional application No. 60/549,347, filed on Mar. 2, 2004, provisional application No. 60/510,406, filed on Oct. 10, 2003, provisional application No. 60/510,411, filed on Oct. 10, 2003, provisional application No. 60/510,450, filed on Oct. 10, 2003, provisional application No. 60/480,096, filed on Jun. 20, 2003, provisional application No. 60/480,024, filed on Jun. 20, 2003.

(30) Foreign Application Priority Data

| Jun. 19, 2003 | (DK) | ............................... | 2003 00912 |
| Jun. 19, 2003 | (DK) | ............................... | 2003 00913 |
| Oct. 10, 2003 | (DK) | ............................... | 2003 01492 |
| Oct. 10, 2003 | (DK) | ............................... | 2003 01493 |
| Oct. 10, 2003 | (DK) | ............................... | 2003 01494 |
| Mar. 1, 2004 | (DK) | ............................... | 2004 00331 |
| Mar. 1, 2004 | (DK) | ............................... | 2004 00332 |
| Mar. 1, 2004 | (DK) | ............................... | 2004 00333 |

(51) Int. Cl.
*C12N 9/48* (2006.01)
*C07H 21/04* (2006.01)
*A21D 2/00* (2006.01)
*A21D 8/02* (2006.01)
*C11C 3/00* (2006.01)

(52) U.S. Cl. ...................... 435/212; 536/23.2; 426/20; 510/300

(58) Field of Classification Search ...................... None
See application file for complete search history.

(56) References Cited

FOREIGN PATENT DOCUMENTS

| DE | 200432 | 5/1983 |
| JP | 02255081 | 10/1990 |
| JP | 2003284571 | 10/2003 |
| WO | WO 88/03947 | 6/1988 |
| WO | WO 01/58276 | 8/2001 |
| WO | WO 2004/07221 | 8/2004 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
A_Geneseq_Dec. 16, 2004 Database Accession No. AAW92997 May 19, 1999 Novo-Nordisk AS from DK9600013 PD Jan. 9, 1996. Alignment with 167-354 of SEQ ID No. 2.*
A_Geneseq_Dec. 16, 2004 Database Accession No. AAU07125 Oct. 24, 2001 Oestergaard et al from WO200158276 PD Aug. 16, 2001. Alignment with 167-354 of SEQ ID No. 2.*
N_Geneseq_Dec. 16, 2004 Database Accession No. AAX22316 May 19, 1999 Novo-Nordisk AS from DK9600013 PD Jan. 9, 1996. Alignment with 499-1062 of SEQ ID No. 1.*
Tsujibo et al. Purification and characterization of two types of alkaline serine proteases produced by an alkalophilic actinomycete. J Appl Bacteriol. 1990(a) Oct;69(4):520-9.*
Tsujibo et al. Amino acid compositions and partial sequences of two types of alkaline serine proteases from *Nocardiopsis dassonvillei* subsp. prasina OPC-210. Agric Biol Chem. 1990(b) Aug;54(8):2177-9.*
Danish Patent Application No. PA 1996 00013 on "Novel DNA Sequences" (1996).
Mitsuiki et al, Bioscience Biotechnology Biochemistry, vol. 66, Part 1, pp. 164-167 (2002).

* cited by examiner

*Primary Examiner*—Sheridan Swope
(74) *Attorney, Agent, or Firm*—Elias J. Lambiris

(57) ABSTRACT

The present invention relates to thermostable proteases having an amino acid sequence which homologous to the amino acid sequence of proteases derived from *Nocardiopsis*, and the production thereof by wild-type and recombinant host cells including transgenic plants and non-human transgenic animals. The proteases are effective in animal feed, in particular fish feed, and detergents. The proteases are capable of degrading the soybean Bowman-Birk inhibitor, and other antinutritional factors such as soybean agglutinin and the Kunitz trypsin inhibitor, as well as the isolated soy storage proteins glycinin and beta-conglycinin. Characteristic structural features of relevance for the thermostability of these proteases of peptidase family S2A or S1E are disclosed.

20 Claims, No Drawings

SEQUENCE LISTING

<160> NUMBER OF SEQ ID NOS: 12

<210> SEQ ID NO 1
<211> LENGTH: 1065
<212> TYPE: DNA
<213> ORGANISM: Nocardiopsis dassonvillei subsp. dassonvillei DSM 43235
<220> FEATURE:
<221> NAME/KEY: CDS
<222> LOCATION: (1)..(1062)
<220> FEATURE:
<221> NAME/KEY: pro_peptide
<222> LOCATION: (1)..(498)
<220> FEATURE:
<221> NAME/KEY: mat_peptide
<222> LOCATION: (499)..(1062)

<400> SEQUENCE: 1

| | | | | | | | | | | | | | | | |
|---|---|---|---|---|---|---|---|---|---|---|---|---|---|---|---|
| gct | ccg | gcc | ccc | gtc | ccc | cag | acc | ccc | gtc | gcc | gac | gac | agc | gcc | 45 |
| Ala | Pro | Ala | Pro | Val | Pro | Gln | Thr | Pro | Val | Ala | Asp | Asp | Ser | Ala | |
| | -165 | | | -160 | | | | -155 | | | | | | | |
| gcc | agc | atg | acc | gag | gcg | ctc | aag | cgc | gac | ctc | gac | ctc | acc | tcg | 90 |
| Ala | Ser | Met | Thr | Glu | Ala | Leu | Lys | Arg | Asp | Leu | Asp | Leu | Thr | Ser | |
| | -150 | | | | -145 | | | | -140 | | | | | | |
| gcc | gag | gcc | gag | gag | ctt | ctc | tcg | gcg | cag | gaa | gcc | gcc | atc | gag | 135 |
| Ala | Glu | Ala | Glu | Glu | Leu | Leu | Ser | Ala | Gln | Glu | Ala | Ala | Ile | Glu | |
| | -135 | | | | -130 | | | | -125 | | | | | | |
| acc | gac | gcc | gag | gcc | acc | gag | gcc | gcg | ggc | gag | gcc | tac | ggc | ggc | 180 |
| Thr | Asp | Ala | Glu | Ala | Thr | Glu | Ala | Ala | Gly | Glu | Ala | Tyr | Gly | Gly | |
| | -120 | | | | -115 | | | | -110 | | | | | | |
| tca | ctg | ttc | gac | acc | gag | acc | ctc | gaa | ctc | acc | gtg | ctg | gtc | acc | gac | 228 |
| Ser | Leu | Phe | Asp | Thr | Glu | Thr | Leu | Glu | Leu | Thr | Val | Leu | Val | Thr | Asp |
| | -105 | | | | -100 | | | | -95 | | | | | | |
| gcc | tcc | gcc | gtc | gag | gcg | gtc | gag | gcc | acc | gga | gcc | cag | gcc | acc | gtc | 276 |
| Ala | Ser | Ala | Val | Glu | Ala | Val | Glu | Ala | Thr | Gly | Ala | Gln | Ala | Thr | Val |
| -90 | | | | -85 | | | | -80 | | | | -75 | | | |
| gtc | tcc | cac | ggc | acc | gag | ggc | ctg | acc | gag | gtc | gtg | gag | gac | ctc | aac | 324 |
| Val | Ser | His | Gly | Thr | Glu | Gly | Leu | Thr | Glu | Val | Val | Glu | Asp | Leu | Asn |
| | | -70 | | | | -65 | | | | -60 | | | | | |
| ggc | gcc | gag | gtt | ccc | gag | agc | gtc | ctc | ggc | tgg | tac | ccg | gac | gtg | gag | 372 |
| Gly | Ala | Glu | Val | Pro | Glu | Ser | Val | Leu | Gly | Trp | Tyr | Pro | Asp | Val | Glu |
| | -55 | | | | -50 | | | | -45 | | | | | | |
| agc | gac | acc | gtc | gtg | gtc | gag | gtg | ctg | gag | ggc | tcc | gac | gcc | gac | gtc | 420 |
| Ser | Asp | Thr | Val | Val | Val | Glu | Val | Leu | Glu | Gly | Ser | Asp | Ala | Asp | Val |
| | -40 | | | | -35 | | | | -30 | | | | | | |
| gcc | gcc | ctg | ctc | gcc | gac | gcc | ggt | gtg | gac | tcc | tcc | tcg | gtc | cgg | gtg | 468 |
| Ala | Ala | Leu | Leu | Ala | Asp | Ala | Gly | Val | Asp | Ser | Ser | Ser | Val | Arg | Val |
| | -25 | | | | -20 | | | | -15 | | | | | | |
| gag | gag | gcc | gag | gag | gcc | ccg | cag | gtc | tac | gcc | gac | atc | atc | ggc | ggc | 516 |
| Glu | Glu | Ala | Glu | Glu | Ala | Pro | Gln | Val | Tyr | Ala | Asp | Ile | Ile | Gly | Gly |
| -10 | | | | -5 | | | | -1 | 1 | | | | 5 | | |
| ctg | gcc | tac | tac | atg | ggc | ggc | cgc | tgc | tcc | gtc | ggc | ttc | gcc | gcg | acc | 564 |
| Leu | Ala | Tyr | Tyr | Met | Gly | Gly | Arg | Cys | Ser | Val | Gly | Phe | Ala | Ala | Thr |
| | | | 10 | | | | 15 | | | | 20 | | | | |
| aac | agc | gcc | ggt | cag | ccc | ggt | ttc | gtc | acc | gcc | ggc | cac | tgc | ggc | acc | 612 |
| Asn | Ser | Ala | Gly | Gln | Pro | Gly | Phe | Val | Thr | Ala | Gly | His | Cys | Gly | Thr |
| | | 25 | | | | 30 | | | | 35 | | | | | |
| gtc | ggc | acc | ggc | gtg | acc | atc | ggc | aac | ggc | acc | ggc | acc | ttc | cag | aac | 660 |
| Val | Gly | Thr | Gly | Val | Thr | Ile | Gly | Asn | Gly | Thr | Gly | Thr | Phe | Gln | Asn |
| | 40 | | | | 45 | | | | 50 | | | | | | |
| tcg | gtc | ttc | ccc | ggc | aac | gac | gcc | gcc | ttc | gtc | cgc | ggc | acc | tcc | aac | 708 |
| Ser | Val | Phe | Pro | Gly | Asn | Asp | Ala | Ala | Phe | Val | Arg | Gly | Thr | Ser | Asn |

```
ttc acc ctg acc aac ctg gtc tcg cgc tac aac tcc ggc ggc tac cag        756
Phe Thr Leu Thr Asn Leu Val Ser Arg Tyr Asn Ser Gly Gly Tyr Gln
             75                  80                  85 tcg gtg acc ggt acc agc cag gcc ccg gcc ggc tcg gcc gtg tgc cgc        804
Ser Val Thr Gly Thr Ser Gln Ala Pro Ala Gly Ser Ala Val Cys Arg
         90                  95                 100 tcc ggc tcc acc acc ggc tgg cac tgc ggc acc atc cag gcc cgc aac        852
Ser Gly Ser Thr Thr Gly Trp His Cys Gly Thr Ile Gln Ala Arg Asn
             105                 110                 115 cag acc gtg cgc tac ccg cag ggc acc gtc tac tcg ctc acc cgc acc        900
Gln Thr Val Arg Tyr Pro Gln Gly Thr Val Tyr Ser Leu Thr Arg Thr
     120                 125                 130 aac gtg tgc gcc gag ccc ggc gac tcc ggc ggt tcg ttc atc tcc ggc        948
Asn Val Cys Ala Glu Pro Gly Asp Ser Gly Gly Ser Phe Ile Ser Gly
135                 140                 145                 150 tcg cag gcc cag ggc gtc acc tcc ggc ggc tcc ggc aac tgc tcc gtc        996
Ser Gln Ala Gln Gly Val Thr Ser Gly Gly Ser Gly Asn Cys Ser Val
                 155                 160                 165 ggc ggc acg acc tac tac cag gag gtc acc ccg atg atc aac tcc tgg       1044
Gly Gly Thr Thr Tyr Tyr Gln Glu Val Thr Pro Met Ile Asn Ser Trp
             170                 175                 180 ggt gtc agg atc cgg acc taa                                            1065
Gly Val Arg Ile Arg Thr
             185

<210> SEQ ID NO 2
<211> LENGTH: 354
<212> TYPE: PRT
<213> ORGANISM: Nocardiopsis dassonvillei subsp. dassonvillei DSM 43235

<400> SEQUENCE: 2

Ala Pro  Ala Pro Val Pro Gln  Thr Pro Val Ala Asp  Asp Ser Ala
    -165              -160                  -155

Ala Ser  Met Thr Glu Ala Leu  Lys Arg Asp Leu Asp  Leu Thr Ser
    -150              -145                  -140

Ala Glu  Ala Glu Glu Leu Leu  Ser Ala Gln Glu Ala  Ala Ile Glu
    -135              -130                  -125

Thr Asp  Ala Glu Ala Thr Glu  Ala Ala Gly Glu Ala  Tyr Gly Gly
    -120              -115                  -110

Ser Leu  Phe Asp Thr Glu Thr  Leu Glu Leu Thr Val  Leu Val Thr Asp
    -105              -100                   -95

Ala Ser  Ala Val Glu Ala Val  Glu Ala Thr Gly Ala  Gln Ala Thr Val
-90               -85                   -80                   -75

Val Ser  His Gly Thr Glu Gly  Leu Thr Glu Val Val  Glu Asp Leu Asn
             -70                   -65                   -60

Gly Ala  Glu Val Pro Glu Ser  Val Leu Gly Trp Tyr  Pro Asp Val Glu
             -55                   -50                   -45

Ser Asp  Thr Val Val Glu Val  Leu Glu Gly Ser Asp  Ala Asp Val
         -40                   -35                  -30

Ala Ala  Leu Leu Ala Asp Ala  Gly Val Asp Ser Ser  Val Arg Val
         -25                   -20                  -15

Glu Glu  Ala Glu Glu Ala Pro  Gln Val Tyr Ala Asp  Ile Ile Gly Gly
-10                    -5                    -1   1                 5

Leu Ala  Tyr Tyr Met Gly Gly  Arg Cys Ser Val Gly  Phe Ala Ala Thr
              10                    15                   20

Asn Ser Ala Gly Gln Pro Gly Phe Val Thr Ala Gly His Cys Gly Thr
```

```
                25                  30                  35

Val Gly Thr Gly Val Thr Ile Gly Asn Gly Thr Gly Thr Phe Gln Asn
         40                  45                  50

Ser Val Phe Pro Gly Asn Asp Ala Ala Phe Val Arg Gly Thr Ser Asn
 55                  60                  65                  70

Phe Thr Leu Thr Asn Leu Val Ser Arg Tyr Asn Ser Gly Gly Tyr Gln
             75                  80                  85

Ser Val Thr Gly Thr Ser Gln Ala Pro Ala Gly Ser Ala Val Cys Arg
                 90                  95                 100

Ser Gly Ser Thr Thr Gly Trp His Cys Gly Thr Ile Gln Ala Arg Asn
            105                 110                 115

Gln Thr Val Arg Tyr Pro Gln Gly Thr Val Tyr Ser Leu Thr Arg Thr
        120                 125                 130

Asn Val Cys Ala Glu Pro Gly Asp Ser Gly Gly Ser Phe Ile Ser Gly
135                 140                 145                 150

Ser Gln Ala Gln Gly Val Thr Ser Gly Gly Ser Gly Asn Cys Ser Val
                155                 160                 165

Gly Gly Thr Thr Tyr Tyr Gln Glu Val Thr Pro Met Ile Asn Ser Trp
            170                 175                 180

Gly Val Arg Ile Arg Thr
            185

<210> SEQ ID NO 3
<211> LENGTH: 48
<212> TYPE: DNA
<213> ORGANISM: Artificial sequence
<220> FEATURE:
<223> OTHER INFORMATION: primer

<400> SEQUENCE: 3
gcttttagtt catcgatcgc atcggctgct ccggccccg tccccag               48

<210> SEQ ID NO 4
<211> LENGTH: 35
<212> TYPE: DNA
<213> ORGANISM: Artificial sequence
<220> FEATURE:
<223> OTHER INFORMATION: primer

<400> SEQUENCE: 4
gcggatccta ttaggttctg atcctgacac cccag                            35

<210> SEQ ID NO 5
<211> LENGTH: 24
<212> TYPE: DNA
<213> ORGANISM: Artificial sequence
<220> FEATURE:
<223> OTHER INFORMATION: primer

<400> SEQUENCE: 5
caatcgcatg ttcaatccgc tcca                                        24

<210> SEQ ID NO 6
<211> LENGTH: 12
<212> TYPE: DNA
<213> ORGANISM: Artificial sequence
<220> FEATURE:
<223> OTHER INFORMATION: Primer

<400> SEQUENCE: 6
caatcggctc ct                                                     12
```

<210> SEQ ID NO 7
<211> LENGTH: 1164
<212> TYPE: DNA
<213> ORGANISM: Artificial sequence
<220> FEATURE:
<223> OTHER INFORMATION: Synthetic
<220> FEATURE:
<221> NAME/KEY: CDS
<222> LOCATION: (1)..(1164)
<220> FEATURE:
<221> NAME/KEY: sig_peptide
<222> LOCATION: (1)..(81)
<220> FEATURE:
<221> NAME/KEY: pro_peptide
<222> LOCATION: (82)..(576)
<220> FEATURE:
<221> NAME/KEY: mat_peptide
<222> LOCATION: (577)..(1164)

<400> SEQUENCE: 7

```
atg aaa aaa ccg ctg gga aaa att gtc gca agc aca gca ctt ctt       45
Met Lys Lys Pro Leu Gly Lys Ile Val Ala Ser Thr Ala Leu Leu
    -190            -185                -180 att tca gtg gca ttt agc tca tct att gca tca gca gct aca gga       90
Ile Ser Val Ala Phe Ser Ser Ser Ile Ala Ser Ala Ala Thr Gly
        -175                -170                -165 gca tta ccg cag tct ccg aca ccg gaa gca gat gca gtc tca atg      135
Ala Leu Pro Gln Ser Pro Thr Pro Glu Ala Asp Ala Val Ser Met
            -160                -155                -150 caa gaa gca ctg caa aga gat ctt gat ctt aca tca gca gaa gca      180
Gln Glu Ala Leu Gln Arg Asp Leu Asp Leu Thr Ser Ala Glu Ala
                -145                -140                -135 gaa gaa ctt ctt gct gca caa gat aca gca ttt gaa gtg gat gaa      225
Glu Glu Leu Leu Ala Ala Gln Asp Thr Ala Phe Glu Val Asp Glu
                    -130                -125                -120 gca gcg gca gaa gca gca gga gat gca tat ggc ggc tca gtt ttt      270
Ala Ala Ala Glu Ala Ala Gly Asp Ala Tyr Gly Gly Ser Val Phe
                        -115                -110                -105 gat aca gaa tca ctt gaa ctt aca gtt ctt gtt aca gat gca gca gca  318
Asp Thr Glu Ser Leu Glu Leu Thr Val Leu Val Thr Asp Ala Ala Ala
                            -100                -95                -90 gtt gaa gca gtt gaa gca aca gga gca gga aca gta ctt gtt tca tat  366
Val Glu Ala Val Glu Ala Thr Gly Ala Gly Thr Val Leu Val Ser Tyr
                -85                -80                -75 gga att gat ggc ctt gat gaa att gtt caa gaa ctg aat gca gct gat  414
Gly Ile Asp Gly Leu Asp Glu Ile Val Gln Glu Leu Asn Ala Ala Asp
-70                -65                -60                -55 gct gtt ccg ggc gtt gtt ggc tgg tat ccg gat gtt gct gga gat aca  462
Ala Val Pro Gly Val Val Gly Trp Tyr Pro Asp Val Ala Gly Asp Thr
                    -50                -45                -40 gtt gtc ctt gaa gtt ctt gaa gga tca ggc gca gat gtt tca ggc ctg  510
Val Val Leu Glu Val Leu Glu Gly Ser Gly Ala Asp Val Ser Gly Leu
                        -35                -30                -25 ctg gca gac gca gga gtc gat gca tca gca gtt gaa gtt aca aca tca  558
Leu Ala Asp Ala Gly Val Asp Ala Ser Ala Val Glu Val Thr Thr Ser
                -20                -15                -10 gat caa ccg gaa ctt tat gca gat att att ggc ggc ctg gca tat tat  606
Asp Gln Pro Glu Leu Tyr Ala Asp Ile Ile Gly Gly Leu Ala Tyr Tyr
    -5                -1   1                5                    10 atg ggc ggc aga tgc agc gtt ggc ttt gca gca aca aat gca tca ggc  654
Met Gly Gly Arg Cys Ser Val Gly Phe Ala Ala Thr Asn Ala Ser Gly
                    15                20                25
```

```
caa ccg ggc ttt gtt aca gca ggc cat tgc ggc aca gtt ggc aca cca      702
Gln Pro Gly Phe Val Thr Ala Gly His Cys Gly Thr Val Gly Thr Pro
        30                  35                  40 gtt tca att ggc aat ggc aaa ggc gtt ttt gaa cga agc att ttt ccg      750
Val Ser Ile Gly Asn Gly Lys Gly Val Phe Glu Arg Ser Ile Phe Pro
    45                  50                  55 ggc aat gat tca gca ttt gtt aga ggc aca tca aat ttt aca ctt aca      798
Gly Asn Asp Ser Ala Phe Val Arg Gly Thr Ser Asn Phe Thr Leu Thr
60                  65                  70 aat ctg gtt tca aga tat aat tca ggc ggc tat gca aca gtt gca ggc      846
Asn Leu Val Ser Arg Tyr Asn Ser Gly Gly Tyr Ala Thr Val Ala Gly
75                  80                  85                  90 cat aat caa gca ccg att ggc tca gca gtt tgc aga tca ggc tca aca      894
His Asn Gln Ala Pro Ile Gly Ser Ala Val Cys Arg Ser Gly Ser Thr
            95                  100                 105 aca ggc tgg cat tgc ggc aca att caa gca aga aat caa aca gtt agg      942
Thr Gly Trp His Cys Gly Thr Ile Gln Ala Arg Asn Gln Thr Val Arg
        110                 115                 120 tat ccg caa ggc aca gtt tat agt ctg aca aga aca aca gtt tgt gca      990
Tyr Pro Gln Gly Thr Val Tyr Ser Leu Thr Arg Thr Thr Val Cys Ala
    125                 130                 135 gaa ccg ggc gat tca ggc ggc tca tat att agc ggc act caa gca caa     1038
Glu Pro Gly Asp Ser Gly Gly Ser Tyr Ile Ser Gly Thr Gln Ala Gln
140                 145                 150 ggc gtt aca tca ggc ggc tca ggc aat tgc agt gct ggc ggc aca aca     1086
Gly Val Thr Ser Gly Gly Ser Gly Asn Cys Ser Ala Gly Gly Thr Thr
155                 160                 165                 170 tat tac caa gaa gtt aat ccg atg ctt agt tca tgg ggc ctt aca ctt     1134
Tyr Tyr Gln Glu Val Asn Pro Met Leu Ser Ser Trp Gly Leu Thr Leu
            175                 180                 185 aga aca caa tcg cat gtt caa tcc gct cca                             1164
Arg Thr Gln Ser His Val Gln Ser Ala Pro
        190                 195

<210> SEQ ID NO 8
<211> LENGTH: 388
<212> TYPE: PRT
<213> ORGANISM: Artificial sequence
<220> FEATURE:
<223> OTHER INFORMATION: Synthetic

<400> SEQUENCE: 8

Met Lys Lys  Pro Leu Gly Lys Ile  Val Ala Ser Thr Ala  Leu Leu
        -190              -185                -180

Ile Ser Val  Ala Phe Ser Ser Ser  Ile Ala Ser Ala Ala  Thr Gly
        -175              -170                -165

Ala Leu Pro  Gln Ser Pro Thr Pro  Glu Ala Asp Ala Val  Ser Met
        -160              -155                -150

Gln Glu Ala  Leu Gln Arg Asp Leu  Asp Leu Thr Ser Ala  Glu Ala
        -145              -140                -135

Glu Glu Leu  Leu Ala Ala Gln Asp  Thr Ala Phe Glu Val  Asp Glu
        -130              -125                -120

Ala Ala Ala  Glu Ala Ala Gly Asp  Ala Tyr Gly Gly Ser  Val Phe
        -115              -110                -105

Asp Thr Glu  Ser Leu Glu Leu Thr  Val Leu Val Thr Asp  Ala Ala Ala
        -100              -95                 -90

Val Glu Ala  Val Glu Ala Thr Gly  Ala Gly Thr Val Leu  Val Ser Tyr
        -85               -80                 -75

Gly Ile Asp Gly Leu Asp Glu Ile Val Gln Glu Leu Asn Ala Ala Asp
```

```
              -70                 -65                 -60                 -55
Ala Val Pro Gly Val Gly Trp Tyr Pro Asp Val Ala Gly Asp Thr
                -50                 -45                 -40
Val Val Leu Glu Val Leu Glu Gly Ser Gly Ala Asp Val Ser Gly Leu
                -35                 -30                 -25
Leu Ala Asp Ala Gly Val Asp Ala Ser Ala Val Glu Val Thr Thr Ser
                -20                 -15                 -10
Asp Gln Pro Glu Leu Tyr Ala Asp Ile Ile Gly Gly Leu Ala Tyr Tyr
           -5              -1   1                   5                  10
Met Gly Gly Arg Cys Ser Val Gly Phe Ala Ala Thr Asn Ala Ser Gly
                 15                  20                  25
Gln Pro Gly Phe Val Thr Ala Gly His Cys Gly Thr Val Gly Thr Pro
                 30                  35                  40
Val Ser Ile Gly Asn Gly Lys Gly Val Phe Glu Arg Ser Ile Phe Pro
                 45                  50                  55
Gly Asn Asp Ser Ala Phe Val Arg Gly Thr Ser Asn Phe Thr Leu Thr
         60                  65                  70
Asn Leu Val Ser Arg Tyr Asn Ser Gly Gly Tyr Ala Thr Val Ala Gly
75                  80                  85                  90
His Asn Gln Ala Pro Ile Gly Ser Ala Val Cys Arg Ser Gly Ser Thr
                 95                 100                 105
Thr Gly Trp His Cys Gly Thr Ile Gln Ala Arg Asn Gln Thr Val Arg
                110                 115                 120
Tyr Pro Gln Gly Thr Val Tyr Ser Leu Thr Arg Thr Val Cys Ala
                125                 130                 135
Glu Pro Gly Asp Ser Gly Gly Ser Tyr Ile Ser Gly Thr Gln Ala Gln
        140                 145                 150
Gly Val Thr Ser Gly Gly Ser Gly Asn Cys Ser Ala Gly Gly Thr Thr
155                 160                 165                 170
Tyr Tyr Gln Glu Val Asn Pro Met Leu Ser Ser Trp Gly Leu Thr Leu
                175                 180                 185
Arg Thr Gln Ser His Val Gln Ser Ala Pro
                190                 195
```

<210> SEQ ID NO 9
<211> LENGTH: 1155
<212> TYPE: DNA
<213> ORGANISM: Nocardiopsis sp. DSM 16424
<220> FEATURE:
<221> NAME/KEY: sig_peptide
<222> LOCATION: (1)..(87)
<220> FEATURE:
<221> NAME/KEY: CDS
<222> LOCATION: (1)..(1152)
<220> FEATURE:
<221> NAME/KEY: pro_peptide
<222> LOCATION: (88)..(585)
<220> FEATURE:
<221> NAME/KEY: mat_peptide
<222> LOCATION: (586)..(1152)

<400> SEQUENCE: 9

```
atg aga ccc tcc acc atc gcc tcc gcc gtc ggc aca gga gca ctg      45
Met Arg Pro Ser Thr Ile Ala Ser Ala Val Gly Thr Gly Ala Leu
-195               -190                -185 gcc ttc ggt ctg gca ctg tcc atg gcc ccc gga gcc ctc gcg gcg      90
Ala Phe Gly Leu Ala Leu Ser Met Ala Pro Gly Ala Leu Ala Ala
-180               -175                -170 ccc ggc ccc gtc ccc cag acc ccc gtc gcc gac gac agc gcc gcc     135
```

```
                Pro Gly Pro Val Pro Gln  Thr Pro Val Ala Asp  Asp Ser Ala Ala
                -165         -160                 -155 agc atg acc gaa gcg ctc aag cgt gac ctc aac ctc tcc tcg gcc              180
Ser Met Thr Glu Ala Leu Lys Arg Asp Leu Asn Leu Ser Ser Ala
-150             -145                 -140 gag gcc gag gag ctg ctc tcg gcg cag gaa gcc gcg atc gag acc              225
Glu Ala Glu Glu Leu Leu Ser Ala Gln Glu Ala Ala Ile Glu Thr
-135             -130                 -125 gac gcc gag gcc gcc gag gcc gcg gga gag gcc tac ggc ggc tcc              270
Asp Ala Glu Ala Ala Glu Ala Ala Gly Glu Ala Tyr Gly Gly Ser
-120             -115                 -110 ctg ttc gac acc gaa acc ctc gaa ctc acc gtg ctg gtg acc gac acc          318
Leu Phe Asp Thr Glu Thr Leu Glu Leu Thr Val Leu Val Thr Asp Thr
-105             -100                 -95                  -90 acg gcc gtc gac gcg gtc gag gcc acc gga gcc gag gcc acc gtg gtc          366
Thr Ala Val Asp Ala Val Glu Ala Thr Gly Ala Glu Ala Thr Val Val
                 -85                  -80                  -75 acc cac ggc acc gac ggc ctg gcc gag gtc gtg gag gac ctc aac agc          414
Thr His Gly Thr Asp Gly Leu Ala Glu Val Val Glu Asp Leu Asn Ser
                 -70                  -65                  -60 gcc gac gcc ccg gcg ggc gtc ctc ggc tgg tac ccc gac atg gag agc          462
Ala Asp Ala Pro Ala Gly Val Leu Gly Trp Tyr Pro Asp Met Glu Ser
-55                  -50                  -45 gac acc gtg gtg gtc gag gtg ctg gag ggc tcc gac gcc gac gtc gcc          510
Asp Thr Val Val Val Glu Val Leu Glu Gly Ser Asp Ala Asp Val Ala
    -40                  -35                  -30 gcc ctg ctc gcc gac gcc ggc gtg gac gcc tcc gcc gtc cgg gtg gag          558
Ala Leu Leu Ala Asp Ala Gly Val Asp Ala Ser Ala Val Arg Val Glu
-25                  -20                  -15                  -10 gag gcg gag gag gtc ccg cag gtc tac gcc aac atc atc ggc ggc ctg          606
Glu Ala Glu Glu Val Pro Gln Val Tyr Ala Asn Ile Ile Gly Gly Leu
                 -5                   -1  1                5 gcc tac acc atg ggc gga cgc tgc tcc gtc ggc ttc gcg gcg acc aac          654
Ala Tyr Thr Met Gly Gly Arg Cys Ser Val Gly Phe Ala Ala Thr Asn
             10                  15                  20 agc gcc gga cag ccc ggt ttc gtg acg gcg ggc cac tgc ggc acc gtc          702
Ser Ala Gly Gln Pro Gly Phe Val Thr Ala Gly His Cys Gly Thr Val
25                   30                  35 ggc acc gcc gtg acc atc ggc gac ggc cgc ggc gtc ttc gag cgc tcg          750
Gly Thr Ala Val Thr Ile Gly Asp Gly Arg Gly Val Phe Glu Arg Ser
40                   45                  50                  55 gtc ttc ccc ggc aac gac gcc gcc ttc gtc cgc ggc acc tcc aac ttc          798
Val Phe Pro Gly Asn Asp Ala Ala Phe Val Arg Gly Thr Ser Asn Phe
                 60                  65                  70 acc ctg acc aac ctg gtc tcc cgc tac aac tcc ggc ggc cac cag gcg          846
Thr Leu Thr Asn Leu Val Ser Arg Tyr Asn Ser Gly Gly His Gln Ala
             75                  80                  85 gtg acc ggc acc agc cag gcc ccg gcc ggc tcg gcc gtc tgc cgc tcc          894
Val Thr Gly Thr Ser Gln Ala Pro Ala Gly Ser Ala Val Cys Arg Ser
             90                  95                 100 ggc tcc acc acc ggc tgg cac tgc ggc acc atc cag gcc cgc aac cag          942
Gly Ser Thr Thr Gly Trp His Cys Gly Thr Ile Gln Ala Arg Asn Gln
105                  110                 115 acc gtg cgc tac ccg cag ggc acc gtc aac gcg ctc acc cgc acc aac          990
Thr Val Arg Tyr Pro Gln Gly Thr Val Asn Ala Leu Thr Arg Thr Asn
120                  125                 130                 135 gtg tgc gcc gag ccc ggt gac tcc ggc ggc tcg ttc atc tcc ggc tcg          1038
Val Cys Ala Glu Pro Gly Asp Ser Gly Gly Ser Phe Ile Ser Gly Ser
                 140                 145                 150
```

-continued

```
cag gcc cag ggc gtc acc tcc ggc ggc tcc ggc aac tgc tcc ttc ggc      1086
Gln Ala Gln Gly Val Thr Ser Gly Gly Ser Gly Asn Cys Ser Phe Gly
            155                 160                 165 ggc acg acc tac tac cag gag gtc gcc ccg atg atc aac tcc tgg ggc      1134
Gly Thr Thr Tyr Tyr Gln Glu Val Ala Pro Met Ile Asn Ser Trp Gly
        170                 175                 180 gtt cgc atc cgc acc agc tga                                          1155
Val Arg Ile Arg Thr Ser
    185
```

<210> SEQ ID NO 10
<211> LENGTH: 384
<212> TYPE: PRT
<213> ORGANISM: Nocardiopsis sp. DSM 16424

<400> SEQUENCE: 10

```
Met Arg Pro Ser Thr Ile Ala Ser Ala Val Gly Thr Gly Ala Leu
-195             -190                 -185

Ala Phe Gly Leu Ala Leu Ser Met Ala Pro Gly Ala Leu Ala Ala
-180             -175                 -170

Pro Gly Pro Val Pro Gln Thr Pro Val Ala Asp Asp Ser Ala Ala
-165             -160                 -155

Ser Met Thr Glu Ala Leu Lys Arg Asp Leu Asn Leu Ser Ser Ala
-150             -145                 -140

Glu Ala Glu Glu Leu Leu Ser Ala Gln Glu Ala Ala Ile Glu Thr
-135             -130                 -125

Asp Ala Glu Ala Ala Glu Ala Ala Gly Glu Ala Tyr Gly Gly Ser
-120             -115                 -110

Leu Phe Asp Thr Glu Thr Leu Glu Leu Thr Val Leu Val Thr Asp Thr
-105             -100                 -95                  -90

Thr Ala Val Asp Ala Val Glu Ala Thr Gly Ala Glu Ala Thr Val Val
                 -85                  -80                  -75

Thr His Gly Thr Asp Gly Leu Ala Glu Val Val Glu Asp Leu Asn Ser
             -70                  -65                  -60

Ala Asp Ala Pro Ala Gly Val Leu Gly Trp Tyr Pro Asp Met Glu Ser
         -55                  -50                  -45

Asp Thr Val Val Glu Val Leu Glu Gly Ser Asp Ala Asp Val Ala
     -40                  -35                  -30

Ala Leu Leu Ala Asp Ala Gly Val Asp Ala Ser Ala Val Arg Val Glu
-25                  -20                  -15                  -10

Glu Ala Glu Glu Val Pro Gln Val Tyr Ala Asn Ile Ile Gly Gly Leu
                 -5                   -1  1                5

Ala Tyr Thr Met Gly Gly Arg Cys Ser Val Gly Phe Ala Ala Thr Asn
             10                  15                  20

Ser Ala Gly Gln Pro Gly Phe Val Thr Ala Gly His Cys Gly Thr Val
     25                  30                  35

Gly Thr Ala Val Thr Ile Gly Asp Gly Arg Gly Val Phe Glu Arg Ser
40                   45                  50                  55

Val Phe Pro Gly Asn Asp Ala Ala Phe Val Arg Gly Thr Ser Asn Phe
                 60                  65                  70

Thr Leu Thr Asn Leu Val Ser Arg Tyr Asn Ser Gly Gly His Gln Ala
             75                  80                  85

Val Thr Gly Thr Ser Gln Ala Pro Ala Gly Ser Ala Val Cys Arg Ser
         90                  95                  100

Gly Ser Thr Thr Gly Trp His Cys Gly Thr Ile Gln Ala Arg Asn Gln
    105                 110                 115
```

```
Thr Val Arg Tyr Pro Gln Gly Thr Val Asn Ala Leu Thr Arg Thr Asn
120                 125                 130                 135

Val Cys Ala Glu Pro Gly Asp Ser Gly Gly Ser Phe Ile Ser Gly Ser
                140                 145                 150

Gln Ala Gln Gly Val Thr Ser Gly Gly Ser Gly Asn Cys Ser Phe Gly
            155                 160                 165

Gly Thr Thr Tyr Tyr Gln Glu Val Ala Pro Met Ile Asn Ser Trp Gly
        170                 175                 180

Val Arg Ile Arg Thr Ser
    185

<210> SEQ ID NO 11
<211> LENGTH: 1068
<212> TYPE: DNA
<213> ORGANISM: Nocardiopsis alba DSM 15647
<220> FEATURE:
<221> NAME/KEY: CDS
<222> LOCATION: (1)..(1065)
<220> FEATURE:
<221> NAME/KEY: pro_peptide
<222> LOCATION: (1)..(501)
<220> FEATURE:
<221> NAME/KEY: mat_peptide
<222> LOCATION: (502)..(1065)

<400> SEQUENCE: 11 gcg acc ggc ccc ctc ccc cag tcc ccc acc ccg gat gaa gcc gag        45
Ala Thr Gly Pro Leu Pro Gln Ser Pro Thr Pro Asp Glu Ala Glu
       -165                -160                -155 gcc acc acc atg gtc gag gcc ctc cag cgc gac ctc ggc ctg tcc        90
Ala Thr Thr Met Val Glu Ala Leu Gln Arg Asp Leu Gly Leu Ser
   -150                -145                -140 ccc tct cag gcc gac gag ctc ctc gag gcg cag gcc gag tcc ttc       135
Pro Ser Gln Ala Asp Glu Leu Leu Glu Ala Gln Ala Glu Ser Phe
       -135                -130                -125 gag atc gac gag gcc gcc acc gcg gcc gca gcc gac tcc tac ggc       180
Glu Ile Asp Glu Ala Ala Thr Ala Ala Ala Ala Asp Ser Tyr Gly
   -120                -115                -110 ggc tcc atc ttc gac acc gac agc ctc acc ctg acc gtc ctg gtc acc   228
Gly Ser Ile Phe Asp Thr Asp Ser Leu Thr Leu Thr Val Leu Val Thr
       -105                -100                 -95 gac gcc tcc gcc gtc gag gcg gtc gag gcc gcc ggc gcc gag gcc aag   276
Asp Ala Ser Ala Val Glu Ala Val Glu Ala Ala Gly Ala Glu Ala Lys
    -90                 -85                 -80 gtg gtc tcg cac ggc atg gag ggc ctg gag gag atc gtc gcc gac ctg   324
Val Val Ser His Gly Met Glu Gly Leu Glu Glu Ile Val Ala Asp Leu
-75                 -70                 -65                 -60 aac gcg gcc gac gct cag ccc ggc gtc gtg ggc tgg tac ccc gac atc   372
Asn Ala Ala Asp Ala Gln Pro Gly Val Val Gly Trp Tyr Pro Asp Ile
        -55                 -50                 -45 cac tcc gac acg gtc gtc ctc gag gtc ctc gag ggc tcc ggt gcc gac   420
His Ser Asp Thr Val Val Leu Glu Val Leu Glu Gly Ser Gly Ala Asp
            -40                 -35                 -30 gtg gac tcc ctg ctc gcc gac gcc ggt gtg gac acc gcc gac gtc aag   468
Val Asp Ser Leu Leu Ala Asp Ala Gly Val Asp Thr Ala Asp Val Lys
    -25                 -20                 -15 gtg gag agc acc acc gag cag ccc gag ctg tac gcc gac atc atc ggc   516
Val Glu Ser Thr Thr Glu Gln Pro Glu Leu Tyr Ala Asp Ile Ile Gly
    -10                  -5                  -1   1              5 ggt ctc gcc tac acc atg ggt ggg cgc tgc tcg gtc ggc ttc gcg gcc   564
Gly Leu Ala Tyr Thr Met Gly Gly Arg Cys Ser Val Gly Phe Ala Ala
```

```
                       10                  15                  20
acc aac gcc tcc ggc cag ccc ggg ttc gtc acc gcc ggc cac tgc ggc        612
Thr Asn Ala Ser Gly Gln Pro Gly Phe Val Thr Ala Gly His Cys Gly
             25                  30                  35 acc gtc ggc acc ccg gtc agc atc ggc aac ggc cag ggc gtc ttc gag        660
Thr Val Gly Thr Pro Val Ser Ile Gly Asn Gly Gln Gly Val Phe Glu
         40                  45                  50 cgt tcc gtc ttc ccc ggc aac gac tcc gcc ttc gtc cgc ggc acc tcg        708
Arg Ser Val Phe Pro Gly Asn Asp Ser Ala Phe Val Arg Gly Thr Ser
     55                  60                  65 aac ttc acc ctg acc aac ctg gtc agc cgc tac aac acc ggt ggt tac        756
Asn Phe Thr Leu Thr Asn Leu Val Ser Arg Tyr Asn Thr Gly Gly Tyr
 70                  75                  80                  85 gcg acc gtc tcc ggc tcc tcg cag gcg gcg atc ggc tcg cag atc tgc        804
Ala Thr Val Ser Gly Ser Ser Gln Ala Ala Ile Gly Ser Gln Ile Cys
                 90                  95                 100 cgt tcc ggc tcc acc acc ggc tgg cac tgc ggc acc gtc cag gcc cgc        852
Arg Ser Gly Ser Thr Thr Gly Trp His Cys Gly Thr Val Gln Ala Arg
             105                 110                 115 ggc cag acg gtg agc tac ccc cag ggc acc gtg cag aac ctg acc cgc        900
Gly Gln Thr Val Ser Tyr Pro Gln Gly Thr Val Gln Asn Leu Thr Arg
         120                 125                 130 acc aac gtc tgc gcc gag ccc ggt gac tcc ggc tcc ttc atc tcc            948
Thr Asn Val Cys Ala Glu Pro Gly Asp Ser Gly Ser Phe Ile Ser
     135                 140                 145 ggc agc cag gcc cag ggc gtc acc tcc ggt ggc tcc ggc aac tgc tcc        996
Gly Ser Gln Ala Gln Gly Val Thr Ser Gly Gly Ser Gly Asn Cys Ser
150                 155                 160                 165 ttc ggt ggc acc acc tac tac cag gag gtc aac ccg atg ctg agc agc       1044
Phe Gly Gly Thr Thr Tyr Tyr Gln Glu Val Asn Pro Met Leu Ser Ser
                 170                 175                 180 tgg ggt ctg acc ctg cgc acc tga                                        1068
Trp Gly Leu Thr Leu Arg Thr
             185

<210> SEQ ID NO 12
<211> LENGTH: 355
<212> TYPE: PRT
<213> ORGANISM: Nocardiopsis alba DSM 15647

<400> SEQUENCE: 12

Ala Thr Gly  Pro Leu Pro Gln Ser  Pro Thr Pro Asp Glu  Ala Glu
         -165             -160                 -155

Ala Thr Thr  Met Val Glu Ala Leu  Gln Arg Asp Leu Gly  Leu Ser
         -150             -145                 -140

Pro Ser Gln  Ala Asp Glu Leu Leu  Glu Ala Gln Ala Glu  Ser Phe
         -135             -130                 -125

Glu Ile Asp  Glu Ala Ala Thr Ala  Ala Ala Ala Asp Ser  Tyr Gly
         -120             -115                 -110

Gly Ser Ile  Phe Asp Thr Asp Ser  Leu Thr Leu Thr Val  Leu Val Thr
         -105             -100                  -95

Asp Ala Ser Ala Val Glu Ala Val Glu Ala Ala Gly Ala Glu Ala Lys
         -90              -85                  -80

Val Val Ser His Gly Met Glu Gly Leu Glu Glu Ile Val Ala Asp Leu
-75                  -70                  -65                  -60

Asn Ala Ala Asp Ala Gln Pro Gly Val Val Gly Trp Tyr Pro Asp Ile
             -55                  -50                  -45

His Ser Asp Thr Val Val Leu Glu Val Leu Glu Gly Ser Gly Ala Asp
```

-continued

```
                -40                 -35                 -30
Val Asp Ser Leu Leu Ala Asp Ala Gly Val Asp Thr Ala Asp Val Lys
        -25                 -20                 -15

Val Glu Ser Thr Thr Glu Gln Pro Glu Leu Tyr Ala Asp Ile Ile Gly
    -10                  -5              -1   1                5

Gly Leu Ala Tyr Thr Met Gly Gly Arg Cys Ser Val Gly Phe Ala Ala
                 10                  15                  20

Thr Asn Ala Ser Gly Gln Pro Gly Phe Val Thr Ala Gly His Cys Gly
             25                  30                  35

Thr Val Gly Thr Pro Val Ser Ile Gly Asn Gly Gln Gly Val Phe Glu
         40                  45                  50

Arg Ser Val Phe Pro Gly Asn Asp Ser Ala Phe Val Arg Gly Thr Ser
     55                  60                  65

Asn Phe Thr Leu Thr Asn Leu Val Ser Arg Tyr Asn Thr Gly Gly Tyr
 70              75                  80                      85

Ala Thr Val Ser Gly Ser Ser Gln Ala Ala Ile Gly Ser Gln Ile Cys
             90                  95                 100

Arg Ser Gly Ser Thr Thr Gly Trp His Cys Gly Thr Val Gln Ala Arg
            105                 110                 115

Gly Gln Thr Val Ser Tyr Pro Gln Gly Thr Val Gln Asn Leu Thr Arg
            120                 125                 130

Thr Asn Val Cys Ala Glu Pro Gly Asp Ser Gly Gly Ser Phe Ile Ser
        135                 140                 145

Gly Ser Gln Ala Gln Gly Val Thr Ser Gly Gly Ser Gly Asn Cys Ser
150                 155                 160                 165

Phe Gly Gly Thr Thr Tyr Tyr Gln Glu Val Asn Pro Met Leu Ser Ser
                170                 175                 180

Trp Gly Leu Thr Leu Arg Thr
            185
```

THERMOSTABLE PROTEASES

CROSS-REFERENCE TO RELATED APPLICATIONS

This application claims priority or the benefit under 35 U.S.C. 119 of Danish application Nos. PA 2003 00912 filed Jun. 19, 2003, PA 2003 00913 filed Jun. 19, 2003, PA 2003 01492 filed Oct. 10, 2003, PA 2003 01493 filed Oct. 10, 2003, PA 2003 01494 filed Oct. 10, 2003, PA 2004 00331 filed Mar. 1, 2004, PA 2004 00332 filed Mar. 1, 2004, and PA 2004 00333 filed Mar. 1, 2004, and U.S. provisional application No. 60/480,024 filed Jun. 20, 2003, 60/480,096 filed Jun. 20, 2003, 60/510,406 filed Oct. 10, 2003, 60/510,411 filed Oct. 10, 2003, 60/510,450 filed Oct. 10, 2003, 60/549,347 filed Mar. 2, 2004, 60/549,349 filed Mar. 2, 2004, and 60/549,761 filed Mar. 2, 2004, the contents of which are fully incorporated herein by reference.

REFERENCE TO A SEQUENCE LISTING

This application includes a computer readable form of a Sequence Listing, which is incorporated herein by reference.

BACKGROUND OF THE INVENTION

1. Field of the Invention

The present invention relates to an isolated polypeptide having protease activity and being homologous to *Nocardiopsis* proteases, as well as isolated nucleic acid sequences encoding it. The invention furthermore relates to nucleic acid constructs, vectors, and host cells, including transgenic plants and non-human animals, comprising these nucleic acid sequences, as well as methods for producing and using the protease, in particular within animal feed, for example in fish feed.

The protease of the invention is thermostable, and characteristic structural features of relevance for the thermostability of proteases of peptidase family S2A or S1E are disclosed.

The protease of the invention furthermore effectively degrades the soybean Bowman-Birk inhibitor, as well as other anti-nutritional factors such as soybean agglutinin, and the Kunitz trypsin inhibitor, and also isolated soy storage proteins such as, glycinin and beta-conglycinin.

2. Description of Related Art

Proteases derived from *Nocardiopsis* sp. NRRL 18262 and *Nocardiopsis dassonvillei* NRRL 18133 are disclosed in WO 88/03947. The DNA and amino acid sequences of the protease derived from *Nocardiopsis* sp. NRRL 18262 are shown in DK application no. 1996 00013. WO 01/58276 discloses the use in animal feed of acid-stable proteases related to the protease derived from *Nocardiopsis* sp. NRRL 18262, as well as a protease derived from *Nocardiopsis alba* DSM 14010. These proteases, however, are not thermostable.

JP 2-255081-A discloses a protease derived from *Nocardiopsis* sp. strain OPC-210 (FERM P-10508), however without sequence information. The strain is no longer available, as the deposit was withdrawn.

DD 20043218 discloses a proteolytic preparation derived from *Nocardiopsis dassonvillei* strain ZIMET 43647, however without sequence information. The strain appears to be no longer available.

JP 2003284571-A, published after the first filing date of the present invention, discloses the amino acid sequence and the corresponding DNA sequence of a protease derived from *Nocardiopsis* sp. TOA-1 (FERM P-18676). The sequence has been entered in GENESEQP with no. ADF43564.

Thermostable proteases are described in the prior art, for example a protease from *Thermomonospora fusca* YX is described by Lao and Wilson in Appl. Environ. Microbiol. 62:4256–4259 (1996), and the sequence was filed in the public databases as sptrembl_086984. However, this protease is not homologous to *Nocardiopsis* proteases, as the percentage identity to the proteases of the invention is below 60%.

It is an object of the present invention to provide thermostable proteases that are homologous to *Nocardiopsis* proteases, in particular with a potential for use in animal feed and/or detergents.

SUMMARY OF THE INVENTION

A number of thermostable proteases were isolated and characterized, viz. a protease derived from *Nocardiopsis dassonvillei* subsp. *dassonvillei* DSM 43235 (see SEQ ID NOs: 1 and 2); a synthetic Protease 22 (see SEQ ID NOs: 7 and 8); a protease L2a derived from *Nocardiopsis* sp. DSM 16424 (see SEQ ID NOs: 9 and 10); and Protease 8 derived from *Nocardiopsis alba* DSM 15647 (see SEQ ID NOs: 11 and 12).

In a first aspect, the invention relates to an isolated polypeptide having protease activity, and having a melting temperature ($T_m$) of at least 78° C., as determined by Differential Scanning Calorimetry (DSC) in a 10 mM sodium phosphate, 50 mM sodium chloride buffer, pH 7.0, using a constant scan rate of 1.5° C./min, wherein the polypeptide is selected from the group consisting of: (a) a polypeptide having an amino acid sequence which has a degree of identity to amino acids 1 to 188 of SEQ ID NO: 2, 1 to 196 of SEQ ID NO: 8, 1 to 189 of SEQ ID NO: 10, and/or 1 to 188 of SEQ ID NO: 12 of at least 60%; (b) a polypeptide which is encoded by a nucleic acid sequence which hybridizes under low stringency conditions with either of nucleotides 499–1062 of SEQ ID NO: 1, 577–1164 of SEQ ID NO: 7, 586–1152 of SEQ ID NO: 9, and/or 502–1065 of SEQ ID NO: 11; and (c) a polypeptide which is encoded by a nucleic acid sequence which has a degree of identity to any one of nucleotides 499–1062 of SEQ ID NO: 1, 577–1164 of SEQ ID NO: 7, 586–1152 of SEQ ID NO: 9, and/or 502–1065 of SEQ ID NO: 11 of at least 60%. The invention also relates to isolated nucleic acid sequences encoding such proteases; nucleic acid constructs, vectors, and host cells comprising the nucleic acid sequences; as well as methods for producing and using the proteases, in particular within animal feed.

In a second aspect, the invention relates to:

A. An isolated polypeptide of peptidase family S2A and/or peptidase family S1E having protease activity, and having an amino sequence comprising at least one of the following amino acids at the position indicated: 10Y, 24S, 38T, 42G, 49T, 51T, 53Q, 54N, 82S, 86Q, 87S, 89T, 91T, 92S, 96A, 99A, 118N, 120T, 122R, 125Q, 129Y, 130S, 131L, 135N, 147F, 151S, 165S, 166V, 171Y, 179I, and/or 186I; preferably 10Y, 38T, 82S, 99A, 118N, 120T, 122R, 125Q, 129Y, 130S, 131L, 165S, and/or 171Y; more preferably together with at least one of 95P, 100V, and/or 114I; and/or together with (H35+D61+S143); wherein each position corresponds to a position of SEQ ID NO: 2;

B. The polypeptide of B which comprises at least one of the following amino acids at the position indicated: 38T, 92S, 120T, 125Q, 131L, 135N, 147F, 151S, 165S, and/or 171Y;

C. The polypeptide of A which comprises at least one of the following amino acids at the position indicated: 10Y, 24S, 42G, 49T, 51T, 53Q, 54N, 82S, 86Q, 87S, 89T, 91T, 96A, 99A, 118N, 122R, 129Y, 130S, 166V, 179I, and/or 186I;

D. An isolated polypeptide of peptidase family S2A and/or peptidase family S1E having protease activity, and having an amino sequence comprising at least one of the following amino acids at the position indicated: 25S, 38T, 42P, 44S, 49Q, 54R, 62S, 89S, 91S, 92S, 95A, 99Q, 100I, 114V, 120T, 125Q, 129Q, 131L, 135N, 147F, 151S, 165S, 166F, 171Y, 176N, 179L, 180S, 184L, and/or 185T; preferably 25S, 38T, 42P, 44S, 54R, 62S, 125Q, 131L, 165S, 171Y, 176N, 179L, 180S, 184L, and/or 185T; more preferably together with at least one of 24A, 51V, 53E, 86A, 87T, 96I, and/or 186L; and/or together with (H35+ D61+S143); wherein each position corresponds to a position of SEQ ID NO: 12;

E. The polypeptide of D which comprises at least one of the following amino acids at the position indicated: 38T, 92S, 120T, 125Q, 131L, 135N, 147F, 151S, 165S, and/or 171Y;

F. The polypeptide of D which comprises at least one of the following amino acids at the position indicated: 25S, 42P, 44S, 49Q, 54R, 62S, 89S, 91S, 95A, 99Q, 100I, 114V, 129Q, 166F, 176N, 179L, 180S, 184L, and/or 185T;

G. The polypeptide of any one of A, B, C, D, E, and F which has a Tm of at least 78° C. as measured by DSC in 10 mM sodium phosphate, 50 mM sodium chloride, pH 7.0; and/or a relative activity at pH9 and 80° C. of at least 0.40;

H. The polypeptide of any one of A, B, C, D, E, F, and G which has a percentage of identity of at least 60% to either of amino acids −166 to 188, preferably 1–188, of SEQ ID NO: 2; amino acids −192 to 196, preferably 1–196, of SEQ ID NO: 8; amino acids −195 to 189, preferably 1–189 of SEQ ID NO: 10; and/or to amino acids −167 to −1, preferably 1–188, of SEQ ID NO: 12;

I. The polypeptide of any one of A, B, C, D, E, F, G; and H which is i) a bacterial protease; ii) a protease of the phylum Actinobacteria; iii) of the class Actinobacteria; iv) of the order Actinomycetales v) of the family Nocardiopsaceae; vi) of the genus *Nocardiopsis*; and/or a protease derived from vii) *Nocardiopsis* species such as *Nocardiopsis alba, Nocardiopsis alkaliphila, Nocardiopsis antarctica, Nocardiopsis prasina, Nocardiopsis composta, Nocardiopsis exhalans, Nocardiopsis halophila, Nocardiopsis halotolerans, Nocardiopsis kunsanensis, Nocardiopsis listeri, Nocardiopsis lucentensis, Nocardiopsis metallicus, Nocardiopsis synnemataformans, Nocardiopsis trehalosi, Nocardiopsis tropica, Nocardiopsis umidischolae, Nocardiopsis xinjiangensis,* or *Nocardiopsis dassonvillei*, e.g. a protease derived from *Nocardiopsis antarctica* or *Nocardiopsis dassonvillei.*, for example *Nocardiopsis dassonvillei* DSM 43235, *Nocardiopsis* sp. DSM 16424, or *Nocardiopsis alba* DSM 15647, such as a polypeptide with the amino acid sequence of the mature peptide parts of either of SEQ ID NOs: 2, 8, 10, or 12;

J. An isolated nucleic acid sequence comprising a nucleic acid sequence which encodes the polypeptide of any one of A, B, C, D, E, F, G, H or I;

K. A nucleic acid construct comprising the nucleic acid sequence of J operably linked to one or more control sequences that direct the production of the polypeptide in a suitable expression host;

L. A recombinant expression vector comprising the nucleic acid construct of K;

M. A recombinant host cell comprising the nucleic acid construct of K or the vector of L;

N. A method for producing a polypeptide of any one of A, B, C, D, E, F, G, H, or I, the method comprising: (a) cultivating a recombinant host cell of M to produce a supernatant comprising the polypeptide; and (b) recovering the polypeptide;

O. A transgenic plant, or plant part, capable of expressing the polypeptide of any one of A, B, C, D, E, F, G, H, or I;

P. A transgenic, non-human animal, or products, or elements thereof, being capable of expressing the polypeptide of any one of A, B, C, D, E, F, G, H, or I;

Q. Use of at least one polypeptide as defined in A, B, C, D, E, F, G, H, or I (i) in animal feed; (ii) in the preparation of a composition for use in animal feed; (iii) for improving the nutritional value of an animal feed; (iv) for increasing digestible and/or soluble protein in animal diets; (v) for increasing the degree of hydrolysis of proteins in animal diets; and/or (vi) for the treatment of proteins;

R. An animal feed additive comprising at least one polypeptide as defined in any one of A, B, C, D, E, F, G, H or I; and (a) at least one fat-soluble vitamin, and/or (b) at least one water-soluble vitamin, and/or (c) at least one trace mineral;

S. An animal feed composition, preferably a fish feed, having a crude protein content of 50 to 800 g/kg and comprising at least one polypeptide as defined in any one of A, B, C, D, E, F, G, H, or I; or at least one feed additive of R;

T. A composition comprising at least one polypeptide as defined in any one of claims A, B, C, D, E, F, G, H, or I, together with at least one other enzyme selected from amongst alpha-amylase (EC 3.2.1.1), phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6); as well as U. Use of at least one polypeptide as defined in any one of A, B, C, D, E, F, G, H or I in detergents.

In a third aspect, the invention relates to:

I. An isolated polypeptide having protease activity, which after incubation for four hours at 37° C. and pH 6.5 has degraded at least 36% (preferably at least 40%, 45%, 50%, 55%, 60%, 65%, 70%, 75%, 80%, or at least 81%) of the soybean Bowman-Birk inhibitor, said percentage degradation being determined as 100% minus the percentage intensity of the intact Bowman-Birk inhibitor band on a stained SDS-PAGE (Tris-Glycine 4–20%) gel after the incubation, relative to the intensity of the same band before the incubation, said intensities of said bands being determined by scanning the gel; wherein the polypeptide is selected from the group consisting of: (a) a polypeptide having an amino acid sequence which has a degree of identity to amino acids 1 to 188 of SEQ ID NO: 2, 1 to 196 of SEQ ID NO: 8, 1 to 189 of SEQ ID NO: 10, and/or 1 to 188 of SEQ ID NO: 12 of at least 60%; (b) a polypeptide which is encoded by a nucleic acid sequence which hybridizes under low stringency conditions with either of nucleotides 499–1062 of SEQ ID NO: 1, 577–1164 of SEQ ID NO: 7, 586–1152 of SEQ ID NO: 9, and/or 502–1065 of SEQ ID NO: 11; and (c) a polypeptide which is encoded by a nucleic acid sequence which has a degree of identity to any one of nucleotides 499–1062 of SEQ ID NO: 1, 577–1164 of SEQ ID NO: 7, 586–1152 of SEQ ID NO: 9, and/or 502–1065 of SEQ ID NO: 11 of at least 60%;

II. The polypeptide of I, wherein the incubation takes place in an incubation buffer containing 50 mM dimethyl glutaric acid, 150 mM NaCl, 1 mM $CaCl_2$, 0,01% Triton X-100, pH 6.5;

III. The polypeptide of any one of 1, or 11, wherein, during the incubation, the ratio between the protease polypeptide and the Bowman-Birk inhibitor is 1:10, based on $A_{280}$;

IV. The polypeptide of any one of I, II, or III, wherein the gel is stained with Coomassie Brilliant Blue;

V. The polypeptide of any one of I, II, III, or IV, wherein the Bowman-Birk inhibitor is Sigma T-9777;

VI. The polypeptide of any one of I, II, III, IV, or V, being further capable of degrading at least one of the following purified soy proteins: Soybean agglutinin (SBA), the Kunitz trypsin inhibitor, glycinin, and/or beta-conglycinin, using the principles as described in any one of I, II, III, IV, or V;

VII. The polypeptide of claim VI which has degraded at least one of the purified soy proteins to an extent of at least 10%, preferably at least 20%, 30%, 40%, 50%, 60%, 70%, 80%, 90%, 92%, 94%, 96%, or at least 98%;

VIII. An isolated nucleic acid sequence comprising a nucleic acid sequence which encodes the polypeptide of any one of I, I, III, IV, V, VI, or VII;

IX. An isolated nucleic acid sequence comprising a nucleic acid sequence which encodes a polypeptide having protease activity, which polypeptide, after incubation for four hours at 37° C. and pH 6.5, has degraded at least 36% (preferably at least 40%, 45%, 50%, 55%, 60%, 65%, 70%, 75%, 80%, or at least 81%) of the soybean Bowman-Birk inhibitor, said percentage degradation being determined as 100% minus the percentage intensity of the intact Bowman-Birk inhibitor band on a stained SDS-PAGE (Tris-Glycine 4–20%) gel after the incubation, relative to the intensity of the same band before the incubation, said intensities of said bands being determined by scanning the gel; wherein the nucleic acid sequence (a) hybridizes under low stringency conditions with either of nucleotides 499–1062 of SEQ ID NO: 1, 577–1164 of SEQ ID NO: 7, 586–1152 of SEQ ID NO: 9, and/or 502–1065 of SEQ ID NO: 11; (b) has a degree of identity to any one of nucleotides 499–1062 of SEQ ID NO: 1577–1164 of SEQ ID NO: 7, 586–1152 of SEQ ID NO: 9, and/or 502–1065 of SEQ ID NO: 11 of at least 60%; and/or (c) encodes a polypeptide which has a degree of identity to amino acids 1 to 188 of SEQ ID NO: 2, 1 to 196 of SEQ ID NO: 8, 1 to 189 of SEQ ID NO: 10, and/or 1 to 188 of SEQ ID NO: 12 of at least 60%;

X. A nucleic acid construct comprising the nucleic acid sequence of any one of VIII, or IX, operably linked to one or more control sequences that direct the production of the polypeptide in a suitable expression host;

XI. A recombinant expression vector comprising the nucleic acid construct of X;

XII. A recombinant host cell comprising the nucleic acid construct of X or the vector of XI;

XIII. A method for producing a polypeptide of 1, the method comprising: (a) cultivating a recombinant host cell of XII to produce a supernatant comprising the polypeptide; and (b) recovering the polypeptide;

XIII. A transgenic plant, or plant part, capable of expressing the polypeptide of I;

XIV. A transgenic, non-human animal, or products, or elements thereof, being capable of expressing the polypeptide of I;

XV. A method for producing a polypeptide of 1, the method comprising (a) cultivating any one of the following strains: (i) *Nocardiopsis dassonvillei* subsp. *dassonvillei* DSM 43235, (ii) *Nocardiopsis* sp. DSM 16424, or (iii) *Nocardiopsis alba* DSM 15647; and (b) recovering the polypeptide;

XVI. Use of at least one polypeptide as defined in I (i) in animal feed; (ii) in the preparation of a composition for use in animal feed; (iii) for improving the nutritional value of an animal feed; (iv) for increasing digestible and/or soluble protein in animal diets; (v) for increasing the degree of hydrolysis of proteins in animal diets; and/or (vi) for the treatment of proteins;

XVII. An animal feed additive comprising at least one polypeptide as defined in I; and (a) at least one fat-soluble vitamin, and/or (b) at least one water-soluble vitamin, and/or (c) at least one trace mineral;

IIXX. An animal feed composition having a crude protein content of 50 to 800 g/kg and comprising at least one polypeptide as defined in 1, or at least one feed additive of XVII;

IXX. The feed composition of IIXX which is a fish feed;

XX. A composition comprising at least one polypeptide as defined in 1, together with at least one other enzyme selected from amongst alpha-amylase (EC 3.2.1.1), phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6); as well as XXI. Use of at least one polypeptide as defined in I in detergents.

In a fourth aspect, the invention relates to:

a. An isolated polypeptide having protease activity, selected from the group consisting of:
(a) a polypeptide having an amino acid sequence which has a degree of identity (i) to amino acids 1 to 188 of SEQ ID NO: 2 of at least 85%, (ii) to amino acids 1 to 196 of SEQ ID NO: 8 of at least 85%, (iii) to amino acids 1–189 of SEQ ID NO: 10 of at least 85%, and/or a degree of identity to amino acids 1–188 of SEQ ID NO: 12 of at least 89%; (b) a polypeptide which is encoded by a nucleic acid sequence which hybridizes under medium-high stringency conditions with (i) nucleotides 499–1062 of SEQ ID NO: 1, (ii) nucleotides 577–1164 of SEQ ID NO: 7, (iii) nucleotides 586–1152 of SEQ ID NO: 9, (iv) nucleotides 502–1065 of SEQ ID NO: 11, (v) a subsequence of any one of (i)–(iv) of at least 100 nucleotides; and/or (vi) a complementary strand of any one of (i)–(v); (c) a variant of the polypeptide having an amino acid sequence of (i) amino acids 1 to 188 of SEQ ID NO: 2, (ii) amino acids 1 to 196 of SEQ ID NO: 8, (iii) amino acids 1–189 of SEQ ID NO: 10, or amino acids 1–188 of SEQ ID NO: 12, comprising a substitution, deletion, extension, and/or insertion of one or more amino acids; (d) an allelic variant of (a), (b), or (c); and (e) a fragment of (a), (b), (c), or (d) that has protease activity;

b. An isolated nucleic acid sequence comprising a nucleic acid sequence which
(a) encodes the polypeptide of a; (b) encodes a polypeptide having protease activity, and which hybridizes under medium-high stringency conditions with (i) nucleotides 499–1062 of SEQ ID NO: 1, (ii) nucleotides 577–1164 of SEQ ID NO: 7, (iii) nucleotides 586–1152 of SEQ ID NO: 9, (iv) nucleotides 502–1065 of SEQ ID NO: 11, (v) a subsequence of any one of (i)–(iv) of at least 100 nucleotides; and/or (vi) a complementary strand of any one of (i)–(v); and/or (c) encodes a polypeptide having protease activity and which has a degree of identity (i) to nucleotides 499–1062 of SEQ ID NO: 1 of at least 86%, (ii) to nucleotides 577–1164 of SEQ ID NO: 7 of at least 65%, (iii) to nucleotides 586–1152 of SEQ ID NO: 9 of at least 85%, (iv) to nucleotides 502–1065 of SEQ ID NO: 11 of at least 89%;

c. An isolated nucleic acid sequence produced by (a) hybridizing a DNA under medium-high stringency conditions with (i) nucleotides 499–1062 of SEQ ID NO: 1, (ii) nucleotides 577–1164 of SEQ ID NO: 7, (iii) nucleotides 586–1152 of SEQ ID NO: 9, (iv) nucleotides 502–1065 of SEQ ID NO: 11, (v) a subsequence of any one of (i)–(iv) of at least 100 nucleotides; and/or (vi) a complementary strand of any one of (i)–(v); and (b) isolating the nucleic acid sequence;

d. A nucleic acid construct comprising the nucleic acid sequence of any one of b, or c, operably linked to one or more control sequences that direct the production of the polypeptide in a suitable expression host;

e. A recombinant expression vector comprising the nucleic acid construct of d;

f. A recombinant host cell comprising the nucleic acid construct of d or the vector of e;

g. A method for producing a polypeptide of a, the method comprising: (a) cultivating a recombinant host cell of f to produce a supernatant comprising the polypeptide; and (b) recovering the polypeptide;

h. A transgenic plant, or plant part, capable of expressing the polypeptide of a;

i. A transgenic, non-human animal, or products, or elements thereof, being capable of expressing the polypeptide of a;

j. A method for producing a polypeptide of a, the method comprising (a) cultivating any one of the following strains: (i) *Nocardiopsis dassonvillei* subsp. *dassonvillei* DSM 43235, (ii) *Nocardiopsis* sp. DSM 16424, or *Nocardiopsis alba* DSM 15647; and (b) recovering the polypeptide;

k. Use of at least one polypeptide as defined in a (i) in animal feed; (ii) in the preparation of a composition for use in animal feed; (iii) for improving the nutritional value of an animal feed; (iv) for increasing digestible and/or soluble protein in animal diets; (v) for increasing the degree of hydrolysis of proteins in animal diets; and/or (vi) for the treatment of proteins;

l. An animal feed additive comprising at least one polypeptide as defined in a; and (a) at least one fat-soluble vitamin, and/or (b) at least one water-soluble vitamin, and/or (c) at least one trace mineral;

m. An animal feed composition having a crude protein content of 50 to 800 g/kg and comprising at least one polypeptide as defined in a, or at least one feed additive of l;

n. The feed composition of m which is a fish feed;

o. A composition comprising at least one polypeptide as defined in a, together with at least one other enzyme selected from amongst alpha-amylase (EC 3.2.1.1), phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6); as well as p. Use of at least one polypeptide as defined in a in detergents.

In a fifth aspect, the invention relates to: an isolated polypeptide having protease activity, selected from the group consisting of: (a) a polypeptide having an amino acid sequence which has a degree of identity to amino acids 1 to 188 of SEQ ID NO: 2, 1 to 188 of SEQ ID NO: 8, 1 to 196 of SEQ ID NO: 8, and/or to of at least 84%; (b) a polypeptide having an amino acid sequence which has a degree of identity to amino acids −166 to 188 of SEQ ID NO: 2, and/or −192 to 196 of SEQ ID NO: 8, of at least 75%; (c) a polypeptide which is encoded by a nucleic acid sequence which hybridizes under medium-high stringency conditions with (i) DNA encoding a protease obtainable from genomic DNA from *Nocardiopsis dassonvillei* subspecies *dassonvillei* DSM 43235 by use of primers SEQ ID NOs: 3 and 4; (ii) nucleotides 499–1062 of SEQ ID NO: 1, and/or 577–1164 of SEQ ID NO: 7; (iii) nucleotides 1–1062 of SEQ ID NO: 1, and/or 1–1164 of SEQ ID NO: 7; (iv) a subsequence of (i) or (ii) or (iii) of at least 100 nucleotides; and/or (v) a complementary strand of (i), (ii), (iii) or (iv); (d) a variant of the polypeptide having an amino acid sequence of amino acids 1 to 188, or −166 to 188 of SEQ ID NO: 2, or amino acids 1 to 196, or −192 to 196 of SEQ ID NO: 8, comprising a substitution, deletion, extension, and/or insertion of one or more amino acids; (e) an allelic variant of (a), (b) or (c); and (f) a fragment of (a), (b), (c), (d) or (e) that has protease activity;

An isolated polypeptide having protease activity, and having a melting temperature ($T_m$) of at least 78° C., as determined by Differential Scanning Calorimetry (DSC) in a 10 mM sodium phosphate, 50 mM sodium chloride buffer, pH 7.0, using a constant scan rate of 1.5° C./min, wherein the polypeptide is selected from the group consisting of: (a) a polypeptide having an amino acid sequence which has a degree of identity to amino acids 1 to 188 of SEQ ID NO: 2, 1 to 188 of SEQ ID NO: 8, and/or 1 to 196 of SEQ ID NO: 8, of at least 50%; (b) a polypeptide having an amino acid sequence which has a degree of identity to amino acids −166 to 188 of SEQ ID NO: 2, and/or −192 to 196 of SEQ ID NO: 8, of at least 50%; (c) a polypeptide which is encoded by a nucleic acid sequence which hybridizes under low stringency conditions with DNA encoding a protease obtainable from genomic DNA from *Nocardiopsis dassonvillei* subspecies *dassonvillei* DSM 43235 by use of primers SEQ ID NOS. 3 and 4; nucleotides 499–1062 of SEQ ID NO: 1, and/or 577–1164 of SEQ ID NO: 7; nucleotides 1–1062 of SEQ ID NO: 1, and/or 1–1164 of SEQ ID NO: 7; a subsequence of (i) or (ii) or (iii) of at least 100 nucleotides; and/or a complementary strand of (i), (ii), (iii) or (iv); (d) a variant of the polypeptide having an amino acid sequence of amino acids 1 to 188, or −166 to 188 of SEQ ID NO: 2, or amino acids 1 to 196, or −192 to 196 of SEQ ID NO: 8, comprising a substitution, deletion, extension, and/or insertion of one or more amino acids; (e) an allelic variant of (a), (b) or (c); and (f) a fragment of (a), (b), (c), (d) or (e) that has protease activity;

An isolated nucleic acid sequence comprising a nucleic acid sequence which (a) encodes the polypeptide of claim 1; (b) encodes a polypeptide having protease activity, and which hybridizes under medium-high stringency conditions with (i) DNA encoding a protease obtainable from genomic DNA from *Nocardiopsis dassonvillei* subspecies *dassonvillei* DSM 43235 by use of primers SEQ ID NOS. 3 and 4; (ii)

nucleotides 499–1062 or 1–1062 of SEQ ID NO: 1, and/or 577–1164 or 1–1164 of SEQ ID NO: 7; (iii) a subsequence of (i) or (ii) of at least 100 nucleotides; and/or (iv) a complementary strand of (i), (ii), or (iii); (c) encodes a polypeptide having protease activity and which has a degree of identity to nucleotides 499–1062 SEQ ID NO: 1, and/or 577–1164 of SEQ ID NO: 7, of at least 85%; and/or (d) encodes a polypeptide having protease activity and which has a degree of identity to nucleotides 1–1062 SEQ ID NO: 1, and/or nucleotides 1–1164 of SEQ ID NO: 7, of at least 81%;

An isolated nucleic acid sequence comprising a nucleic acid sequence which encodes a polypeptide having protease activity and a melting temperature ($T_m$) of at least 78° C., as determined by Differential Scanning Calorimetry (DSC) in a 10 mM sodium phosphate, 50 mM sodium chloride buffer, pH 7.0, using a constant scan rate of 1.5° C./min, wherein the nucleic acid sequence (a) encodes the above polypeptide; (b) hybridizes under low stringency conditions with DNA encoding a protease obtainable from genomic DNA from *Nocardiopsis dassonvillei* subspecies *dassonvillei* DSM 43235 by use of primers SEQ ID NOs: 3 and 4; nucleotides 499–1062 or 1–1062 of SEQ ID NO: 1, and/or 577–1164 or 1–1164 of SEQ ID NO: 7; a subsequence of (i) or (ii) of at least 100 nucleotides; and/or a complementary strand of (i), (ii), or (iii); (c) has a degree of identity to nucleotides 499–1062 of SEQ ID NO: 1, and/or 577–1164 of SEQ ID NO: 7, of at least 50%; and/or (d) has a degree of identity to nucleotides 1–1062 of SEQ ID NO: 1, and/or 1–1164 of SEQ ID NO: 7, of at least 50%;

An isolated nucleic acid sequence produced by (a) hybridizing a DNA under medium-high stringency conditions with DNA encoding a protease obtainable from genomic DNA from *Nocardiopsis dassonvillei* subspecies *dassonvillei* DSM 43235 by use of primers SEQ ID NOS. 3 and 4; nucleotides 499–1062 or 1–1062 of SEQ ID NO: 1, and/or 577–1164 or 1–1164 of SEQ ID NO: 7; a subsequence of (i) or (ii) of at least 100 nucleotides; or a complementary strand of (i), (ii) or (iii); and (b) isolating the nucleic acid sequence;

A nucleic acid construct comprising the above nucleic acid sequence operably linked to one or more control sequences that direct the production of the polypeptide in a suitable expression host;

A recombinant expression vector comprising the nucleic acid construct;

A recombinant host cell comprising the nucleic acid construct or the vector;

A method for producing the above polypeptide, the method comprising: (a) cultivating a recombinant host cell of claim 8 to produce a supernatant comprising the polypeptide; and (b) recovering the polypeptide;

A transgenic plant, or plant part, capable of expressing the above polypeptide;

A transgenic, non-human animal, or products, or elements thereof, being capable of expressing the above polypeptide;

Use of at least one of the above polypeptides (i) in animal feed; (ii) in the preparation of a composition for use in animal feed; (iii) for improving the nutritional value of an animal feed; (iv) for increasing digestible and/or soluble protein in animal diets; (v) for increasing the degree of hydrolysis of proteins in animal diets; and/or (vi) for the treatment of proteins;

An animal feed additive comprising at least one polypeptide as defined above; and (a) at least one fat-soluble vitamin, and/or (b) at least one water-soluble vitamin, and/or (c) at least one trace mineral;

An animal feed composition having a crude protein content of 50 to 800 g/kg and comprising at least one polypeptide as defined above, or at least one feed additive;

A composition comprising at least one polypeptide as defined above, together with at least one other enzyme selected from amongst alpha-amylase (EC 3.2.1.1), phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6);

Use of at least one polypeptide as defined above in detergents;

An isolated polypeptide of peptidase family S2A and/or peptidase family S1E having protease activity, and having an amino sequence comprising at least one of the following amino acids at the position indicated: 10Y, 24S, 38T, 42G, 49T, 51T, 53Q, 54N, 82S, 86Q, 87S, 89T, 91T, 92S, 96A, 99A, 118N, 120T, 122R, 125Q, 129Y, 130S, 131L, 135N, 147F, 151S, 165S, 166V, 171Y, 179I, and/or 186I; preferably 10Y, 38T, 82S, 95P, 99A, 100V, 114I, 118N, 120T, 122R, 125Q, 129Y, 130S, 131L, 165S, and/or 171Y; more preferably together with at least one of 95P, 100V, and/or 114I; and/or together with (H35+D61+S143); wherein each position corresponds to a position of SEQ ID NO: 2;

The above family S2A or S1E polypeptide which comprises at least one of the following amino acids at the position indicated: 38T, 92S, 120T, 125Q, 131L, 135N, 147F, 151S, 165S, and/or 171Y;

The above family S2A or S1E polypeptide which comprises at least one of the following amino acids at the position indicated: 10Y, 24S, 42G, 49T, 51T, 53Q, 54N, 82S, 86Q, 87S, 89T, 91T, 96A, 99A, 118N, 122R, 129Y, 130S, 166V, 179I, and/or 186I;

The above family S2A or S1E polypeptide which has a Tm of at least 78° C. as measured by DSC in 10 mM sodium phosphate, 50 mM sodium chloride, pH 7.0; and/or a relative activity at pH 9 and 80° C. of at least 0.40;

The above family S2A or S1E polypeptide which has a percentage of identity to amino acids 1–188, or –166 to 188, of SEQ ID NO: 2, and/or to amino acids 1–196, or –192 to 196, of SEQ ID NO: 8, of at least 50%;

The above family S2A or S1E polypeptide which is i) a bacterial protease; ii) a protease of the phylum Actinobacteria; iii) of the class Actinobacteria; iv) of the order Actinomycetales v) of the family Nocardiopsaceae; vi) of the genus *Nocardiopsis*; and/or a protease derived from vii) *Nocardiopsis* species such as *Nocardiopsis alba*, *Nocardiopsis antarctica*, *Nocardiopsis prasina*, *Nocardiopsis composta*, *Nocardiopsis exhalans*, *Nocardiopsis halophila*, *Nocardiopsis halotolerans*, *Nocardiopsis kunsanensis*, *Nocardiopsis listeri*, *Nocardiopsis lucentensis*, *Nocardiopsis metallicus*, *Nocardiopsis synnemataformans*, *Nocardiopsis trehalosi*, *Nocardiopsis tropica*, *Nocardiopsis umidischolae*, *Nocardiopsis xinjiangensis*, or *Nocardiopsis dassonvillei*, e.g. a protease derived from *Nocardiopsis antarctica* or *Nocardiopsis dassonvillei*., for example *Nocardiopsis dassonvillei* DSM 43235, such as a polypeptide with the amino acid sequence of amino acids 1 to 188, or –166 to 188, of SEQ ID NO: 2;

An isolated nucleic acid sequence comprising a nucleic acid sequence which encodes the above family S2A or S1E polypeptide;

A nucleic acid construct comprising the nucleic acid sequence operably linked to one or more control sequences that direct the production of the polypeptide in a suitable expression host;

A recombinant expression vector comprising the nucleic acid construct;

A recombinant host cell comprising the nucleic acid construct or the vector;

A method for producing the above family S2A or S1E polypeptide, the method comprising: (a) cultivating a recombinant host cell to produce a supernatant comprising the polypeptide; and (b) recovering the polypeptide;

A transgenic plant, or plant part, capable of expressing the above family S2A or S1E polypeptide;

A transgenic, non-human animal, or products, or elements thereof, being capable of expressing the above family S2A or S1E polypeptide;

Use of at least one of the above S2A or S1E polypeptides (i) in animal feed; (ii) in the preparation of a composition for use in animal feed; (iii) for improving the nutritional value of an animal feed; (iv) for increasing digestible and/or soluble protein in animal diets; (v) for increasing the degree of hydrolysis of proteins in animal diets; and/or (vi) for the treatment of proteins;

An animal feed additive comprising at least one one of the above S2A or S1E polypeptides; and (a) at least one fat-soluble vitamin, and/or (b) at least one water-soluble vitamin, and/or (c) at least one trace mineral;

An animal feed composition having a crude protein content of 50 to 800 g/kg and comprising at least one one of the above S2A or S1E polypeptides, or at least one above feed additive;

A composition comprising at least one one of the above S2A or S1E polypeptides, together with at least one other enzyme selected from amongst alpha-amylase (EC 3.2.1.1); phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6); as well as Use of at least one one of the above S2A or S1E polypeptides in detergents.

The above second, third, fourth, and fifth aspects, are, independently of each other, also preferred sub-aspects of the first aspect of the invention, as well as preferred sub-aspects of each other.

DETAILED DESCRIPTION OF THE INVENTION

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1–5 published in Eur. J. Biochem. 1994, 223,1–5; Eur. J. Biochem. 1995, 232, 1–6; Eur. J. Biochem. 1996, 237, 1–5; Eur. J. Biochem. 1997, 250, 1–6; and Eur. J. Biochem. 1999, 264, 610–650; respectively. The nomenclature is regularly supplemented and updated; see e.g. the World Wide Web (WWW) at www.chem.qmw.ac.uk/iubmb/enzyme/index.html.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In particular embodiments, the proteases of the invention and for use according to the invention are selected from the group consisting of:

(a) Proteases belonging to the EC 3.4.-.- enzyme group;

(b) Serine proteases belonging to the S group of the above Handbook;

(c) Serine proteases of peptidase family S2A; and/or (d) Serine proteases of peptidase family S1E as described in Biochem. J. 290:205–218 (1993) and in MEROPS protease database, release 6.20, Mar. 24, 2003, (www.merops.ac.uk). The database is described in Rawlings, N. D., O'Brien, E. A. & Barrett, A. J. (2002) MEROPS: the protease database. Nucleic Acids Res. 30, 343–346.

For determining whether a given protease is a Serine protease, and a family S2A protease, reference is made to the above Handbook and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C.

Examples of protease substrates are casein, such as Azurine-Crosslinked Casein (AZCL-casein). Two protease assays are described in Example 2 herein, either of which can be used to determine protease activity. For the purposes of this invention, the so-called pNA Assay is a preferred assay.

There are no limitations on the origin of the protease of the invention and/or for use according to the invention. Thus, the term protease includes not only natural or wild-type proteases obtained from microorganisms of any genus, but also any mutants, variants, fragments etc. thereof exhibiting protease activity, as well as synthetic proteases, such as shuffled proteases, and consensus proteases. Such genetically engineered proteases can be prepared as is generally known in the art, e.g. by Site-directed Mutagenesis, by PCR (using a PCR fragment containing the desired mutation as one of the primers in the PCR reactions), or by Random Mutagenesis. The preparation of consensus proteins is described in e.g. EP 897985. Gene shuffling is generally described in e.g. WO 95/22625 and WO 96/00343. Recombination of protease genes can be made independently of the specific sequence of the parents by synthetic shuffling as described in Ness, J. E. et al, in Nature Biotechnology, Vol. 20 (12), pp. 1251–1255, 2002. Synthetic oligonucleotides degenerated in their DNA sequence to provide the possibility of all amino acids found in the set of parent proteases are designed and the genes assembled according to the reference. The shuffling can be carried out for the full length sequence or for only part of the sequence and then later combined with the rest of the gene to give a full length sequence. The proteases of the mature peptide parts of SEQ ID NOs: 2, 8, 10 and 12, such as Protease 22 (SEQ ID NO: 8), and the protease derived from *Nocardiopsis dassonvillei* subspecies *dassonvillei* DSM 43235 (SEQ ID NO: 2), are particular examples of such parent proteases which can be subjected to shuffling as described above, if desired together with the protease derived from *Nocardiopsis* sp. NRRL 18262, to provide additional proteases of the invention. The term "obtained from" as used herein in connection with a given source shall mean that the polypeptide encoded by the nucleic acid sequence is produced by the source or by a cell in which the nucleic acid sequence from the source is present. In a preferred embodiment, the polypeptide is secreted extracellularly.

In a specific embodiment, the protease is a low-allergenic variant, designed to invoke a reduced immunological response when exposed to animals, including man. The term immunological response is to be understood as any reaction by the immune system of an animal exposed to the protease. One type of immunological response is an allergic response leading to increased levels of IgE in the exposed animal. Low-allergenic variants may be prepared using techniques known in the art. For example the protease may be conjugated with polymer moieties shielding portions or epitopes of the protease involved in an immunological response. Conjugation with polymers may involve in vitro chemical coupling of polymer to the protease, e.g. as described in WO 96/17929, WO 98/30682, WO 98/35026, and/or WO 99/00489. Conjugation may in addition or alternatively thereto involve in vivo coupling of polymers to the protease. Such conjugation may be achieved by genetic engineering of the nucleotide sequence encoding the protease, inserting consensus sequences encoding additional glycosylation sites in the protease and expressing the protease in a host capable of glycosylating the protease, see e.g. WO 00/26354. Another way of providing low-allergenic variants is genetic engineering of the nucleotide sequence encoding the protease so as to cause the protease to self-oligomerize, effecting that protease monomers may shield the epitopes of other protease monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the protease by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

A polypeptide according to either aspect of the present invention may comprise an amino acid sequence which has a degree of identity to the mature peptide part of either of SEQ ID NOs: 2, 8, 10, or 12, for example amino acids 1 to 188 of SEQ ID NO: 2, and/or to amino acids 1 to 196 of SEQ ID NO: 8 (the mature peptide parts), of, for example, at least about 60%, and which have protease activity (hereinafter "homologous polypeptides"). In particular embodiments, the degree of identity to either of the mature peptide parts of either of SEQ ID NOs: 2, 8, 10 or 12 is at least about 62%, 64%, 66%, 68%, 70%, 72%, 74%, 76%, 80%, 81%, 82%, 83%, 84%, 85%, 86%, 87%, 88%, 89%, 90%, 91%, 92%, 93%, 94%, 95%, 96%, 97%, 98%, or at least 99%. In alternative embodiments, the degree of identity is at least about 50%, 51%, 52%, 53%, 54%, 55%, 56%, 57%, 58%, or at least about 59%.

In particular embodiments, the polypeptides of the invention i) have; or ii) consist of an amino acid sequence with any of the degrees of identity as mentioned above.

For the purposes of the present invention, the degree of identity between two amino acid sequences, as well as the degree of identity between two nucleotide sequences, is determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is –12 for polypeptides and –16 for nucleotides. The penalties for further residues of a gap are –2 for polypeptides, and –4 for nucleotide.

"Align" is part of the FASTA package version v20u6 (see W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA," Methods in Enzymology 183:63–98). FASTA protein alignments use the Smith-Waterman algorithm with no limitation on gap size (see "Smith-Waterman algorithm", T. F. Smith and M. S. Waterman (1981) J. Mol. Biol. 147:195–197).

In a particular embodiment, the mature peptide parts, or predicted or expected mature peptide parts, of the two amino acid sequences are used for the alignment. In the alternative, that part of the sequence, whose identity to the mature peptide part of SEQ ID NO: 2 and/or SEQ ID NO: 8 is being examined, is chosen, which according to a multiple alignment made as described below is most similar to the mature peptide part of SEQ ID NO: 2 and/or 8, i.e. the corresponding amino acid residues as identified by the multiple alignment.

In the present context, the basis for numbering amino acid residues or assigning position numbers, cf. the second aspect of the invention, is SEQ ID NO: 2 starting with A1 and ending with T188. In the alternative, the basis is amino acids 1–188 of the protease derived from *Nocardiopsis* sp. NRRL 18262 (SEQ ID NO: 1 as disclosed in WO 01/58276, preferably SEQ ID NO: 1 as disclosed in WO 01/58276 in which A87 is substituted with T87. Proteases may comprise extensions as compared to these reference sequences, e.g. SEQ ID NO: 2, i.e. in the N-terminal, and/or the C-terminal ends thereof. The amino acids of such extensions, if any, are to be numbered as is usual in the art, i.e. for a C-terminal extension: 189, 190, 191 and so forth, and for an N-terminal extension –1, –2, –3 and so forth.

For each amino acid residue in each protease aligned to the reference sequence, e.g. SEQ ID NO: 2, as explained above (for the purposes of determining degree of identity), it is possible to directly and unambiguously assign an amino acid residue in the reference sequence, e.g. SEQ ID NO: 2, to which it corresponds. Corresponding residues are assigned the same position, or number, by reference to, e.g., SEQ ID NO: 2.

For each amino acid residue in another protease, the corresponding position of the reference sequence, e.g. SEQ ID NO: 2, can be found, as follows:

The amino acid sequence of the other protease is designated SEQ X. A position corresponding to position N of SEQ ID NO: 2 is found as follows: SEQ X is aligned with SEQ ID NO: 2 as specified above. From the alignment, the position in sequence SEQ X corresponding to position N of SEQ ID NO: 2 can be clearly and unambiguously derived, using the principles described below.

SEQ X may be a mature part of the protease in question, or it may also include a signal peptide part, or it may be a fragment of the mature protease which has protease activity, e.g. a fragment of the same length as SEQ ID NO: 2, and/or it may be the fragment which extends from A1 to T188 when aligned with SEQ ID NO: 2 as described herein.

Three alignments are inserted below as Tables I, II and III. The alignments were prepared as described above, aligning the mature part of another protease (SEQ ID NO: 13, SEQ ID NO: 14, and SEQ ID NO: 15, respectively) to SEQ ID NO: 2. Approximately 50 amino acid residues of each protease are shown.

Looking first at the alignment of Table I, it is clear that, e.g., G42 of SEQ ID NO: 2 corresponds to P42 of SEQ ID NO: 13, as these residues are on top of each other in the alignment. They are both assigned number 42, viz. the number of the corresponding residue in SEQ ID NO: 2. It is also apparent from this alignment that, e.g., SEQ ID NO: 13 does not comprise 10Y, but it does comprise 38T.

The interval scanned may be from 20 to 100C.

There are no upper limitations on the $T_m$, however, it is presently contemplated that the $T_m$ may be below 150° C., 145° C., 140° C., 135° C., 130° C., 125° C., 120° C., 115° C., 110C., 105° C., or below 100° C.

In an alternative embodiment, another buffer is selected for the scanning, e.g. a buffer of pH 5.0, 5.5, 6.0, or pH 6.5.

In further alternative embodiments, a higher or lower scan rate may be used, e.g. a lower one of 1.4° C./min, 1.3° C./min, 1.2° C./min, 1.1° C./min, 1.0° C./min, or 0.9° C./min.

Reference is made to Example 2 for further details about the scanning procedure.

In a particular embodiment, the protease of the invention exhibits an amended temperature activity profile as compared to the protease derived from *Nocardiopsis* sp. NRRL 18262. For example, the protease of the invention may exhibit a relative activity at pH 9 and 80° C. of at least 0.40, preferably at least 0.45, 0.50, 0.55, 0.60, 0.65, 0.70, 0.75, 0.80, 0.85, 0.90, or at least 0.95, the term "relative" referring to the maximum activity measured for the protease in question. For Protease 22, the L2a protease, as well as for the

TABLE I

```
ADIIGGLAYY MGGRCSVGFA ATNSAGQPGF VTAGHCGTVG TGVTIGNGTG   SEQ ID NO: 2

ADIIGGLAYT MGGRCSVGFA ATNASGQPGF VTAGHCGTVG TPVSIGNGQG   SEQ X1
        10         20         30         40         50
```

Tables II and III are examples of alignments producing gaps in either of the two sequences.

In the alignment of Table II, a gap is produced in SEQ ID NO: 14. The highlighted amino acid residue P of SEQ ID NO: 14 is, for the present purposes, designated P28, although in SEQ ID NO: 14 as such it is P25.

protease derived from *Nocardiopsis dassonvillei* subspecies *dassonvillei* DSM 43235, the activity is relative to the activity at 80° C. which is set to 1.000 (100%), and for Protease 8, and the protease derived from *Nocardiopsis* sp. NRRL 18262, the activity at 70° C. is set to 1.000 (100%), see Examples 2, 7, 8, and 9. As another example, the

TABLE II

```
ADIIGGLAYY MGGRCSVGFA ATNSAGQPGF VTAGHCGTVG TGVTIGNGTG   SEQ ID NO: 2

ADIIGGLAYT MGGRCSVGFA ATNA---PGF VTAGHCGTVG TPVSIGNGQG   SEQ X2
        10         20         30         40         50
```

In the alignment of Table III, a gap is produced in SEQ ID NO: 2. When a gap is produced between amino acids having position number nn and (nn+1) of SEQ ID NO: 2, each position of the gap is assigned a lower case or subscript letter: a, b, c etc. to the former position number, i.e. nn. Accordingly, each position of the gap is numbered nna, nnb etc. The highlighted amino acid residue R of SEQ ID NO: 15 is, for the present purposes, designated R33a, although in SEQ ID NO: 15 as such it is R34.

protease of the invention exhibits a relative activity at pH 9 and 90° C. of at least 0.10, preferably at least 0.15, 0.20, 0.25, 0.30, or of at least 0.35. In a particular embodiment, the protease activity is measured using the Protazyme AK assay of Example 2.

A screening for thermostable proteases related to SEQ ID NOs: 2, 8, 10 or 12 of the invention may be performed as follows: Screening a DNA library with primers, e.g. either of SEQ ID NOs: 3 or 4, or preferably with the mature peptide

TABLE III

```
ADIIGGLAYY MGGRCSVGFA ATNSAGQPGF VTA--GHCGT VGTGVTIGNGTG   SEQ ID NO: 2

ADIIGGLAYT MGGRCSVGFA ATNASGQPGF VTARSGHCGT VGTPVSIGNGQG   SEQ X3
        10         20         30         40         50
```

The DSC is performed in a 10 mM sodium phosphate, 50 mM sodium chloride buffer, pH 7.0.

The scan rate is constant, e.g. 1.5° C./min.

encoding parts of either of SEQ ID NOs: 1, 7, 9 or 11; expressing the hybridizing clones in a suitable strain, e.g. a strain of *Bacillus* or *E. coli*. In a next step, the expressed proteases related to either of SEQ ID NOs: 2, 8, 10 and/or 12 are purified, preferably in a micro-purification process (see e.g. WO 03/037914), and the amount of active protease is determined for each candidate by use of the well-known principle of active site titration (AST) with a strong inhibitor of the enzyme. In a subsequent step, a known amount of the enzyme is then incubated at a desired elevated temperature, e.g. 85° C., for a desired time, e.g. 2 hours; and the residual protease activity is determined, e.g. by use of any of the protease assays described herein, for example the Protazyme AK assay of Example 2. The major part of the procedure may be automated, and if desired performed with the assistance of robots. The verification of thermostability is e.g. done by purification of the protease, and establishment of $T_m$ by DSC as described in the experimental part herein.

The present invention also relates to the animal feed use of the polypeptides of the invention.

The degree of identity between two amino acid sequences may also be determined by the Clustal method (Higgins, 1989, CABIOS 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters are Ktuple=1, gap penalty=3, windows=5, and diagonals=5. The degree of identity between two nucleotide sequences may be determined using the same algorithm and software package as described above with the following settings: Gap penalty of 10, and gap length penalty of 10. Pairwise alignment parameters are Ktuple=3, gap penalty=3 and windows=20.

In a particular embodiment, the homologous polypeptides have an amino acid sequence that differs from amino acids 1 to 188 of SEQ ID NO: 2 or −166 to 188 of SEQ ID NO: 2, or from amino acids 1 to 196 of SEQ ID NO: 8 or −192 to 196 of SEQ ID NO: 8, by (i) no more than 75, 74, 73, 72, 71, 70, 69, 68, 67, 66, 65, 64, 63, 62, 62, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or no more than 20 amino acids;

(ii) no more than twenty, nineteen, eighteen, seventeen, sixteen, fifteen, fourteen, thirteen, twelve, or no more than eleven amino acids;

(iii) no more than ten, nine, eight, seven, six, five, four, three, two, or no more than one amino acid;

(iv) ten, or by nine, or by eight, or by seven, or by six, or by five amino acids; or (v) four, or by three, or by two amino acids, or by one amino acid.

In a particular embodiment, the polypeptides of the present invention comprise the amino acid sequence of the mature peptide parts of either of SEQ ID NOs: 2, 8, 10, or 12, or allelic variants thereof; or fragments thereof that have protease activity.

In another preferred embodiment, the polypeptides of the present invention consist of the mature peptide parts of either of SEQ ID NOs: 2, 8, 10, or 12, or allelic variants thereof; or fragments thereof that have protease activity.

A fragment of the mature peptide parts of either of SEQ ID NOs: 2, 8, 10, or 12 is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. The present invention also relates to isolated polypeptides having protease activity and which are encoded by nucleic acid sequences which hybridize under very low, or low, or medium, or medium-high, or high, or very high stringency conditions with a nucleic acid probe which hybridizes under the same conditions with (a) nucleotides 499–1062 of SEQ ID NO: 1, nucleotides 577–1164 of SEQ ID NO: 7, nucleotides 586–1152 of SEQ ID NO: 9, and/or nucleotides 502–1065 of SEQ ID NO: 11; (b) a subsequence of (a), or (c) a complementary strand of (a), or (b) (J. Sambrook, E. F. Fritsch, and T. Maniatis, 1989, Molecular Cloning, A Laboratory Manual, 2nd edition, Cold Spring Harbor, N.Y.). In one particular embodiment the nucleic acid probe is selected from amongst the nucleic acid sequences of (a), (b), or (c) above. The nucleotides of (a) correspond to the mature peptide encoding parts.

The subsequence of the nucleotides mentioned under (a) above may be at least 100 nucleotides, or in another embodiment at least 200 nucleotides. Moreover, the subsequence may encode a polypeptide fragment that has protease activity.

The nucleic acid sequences of (a) or (b) above, as well as the corresponding mature amino acid sequences of SEQ ID NOs: 2, 8, 10, or 12, or a fragment thereof, may be used to design a nucleic acid probe to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^3H$, $^{35}S$, biotin, or avidin). Such probes are encompassed by the present invention.

Thus, a genomic DNA or cDNA library prepared from such other organisms may be screened for DNA that hybridizes with the probes described above and which encodes a polypeptide having protease activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with either of SEQ ID NOs: 1, 7, 9, or 11, or a subsequence thereof, the carrier material is used in a Southern blot. For purposes of the present invention, hybridization indicates that the nucleic acid sequence hybridizes to a labeled nucleic acid probe corresponding to the sequences of (a), (b) or (c) above, under very low to very high stringency conditions. Molecules to which the nucleic acid probe hybridizes under these conditions are detected using X-ray film.

In a particular embodiment, the nucleic acid probe is a nucleic acid sequence which encodes amino acids 1 to 188 of SEQ ID NO: 2, 1 to 196 of SEQ ID NO: 8, 1 to 189 of SEQ ID NO: 10, and/or 1 to 188 of SEQ ID NO: 12, or subsequences thereof. In another embodiment, the nucleic acid probe is nucleotides 499–1062 of SEQ ID NO: 1, 577–1164 of SEQ ID NO: 7, 586–1152 of SEQ ID NO: 9, and/or 502–1065 of SEQ ID NO: 11 (the mature polypeptide coding regions).

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 0.2×SSC, 0.2% SDS, 20% formamide preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes about 15 nucleotides to about 70 nucleotides in length, the carrier material is washed once in 6×SSC plus 0.1% SDS for 15 minutes and twice each for 15 minutes using 6×SSC at 5° C. to 10° C. below the calculated $T_m$.

The present invention also relates to variants of the polypeptide having an amino acid sequence of amino acids 1 to 188 of SEQ ID NO: 2, 1 to 196 of SEQ ID NO: 8, 1 to 189 of SEQ ID NO: 10, and/or 1 to 188 of SEQ ID NO: 12, comprising a substitution, deletion, and/or insertion of one or more amino acids.

The amino acid sequences of the variant polypeptides may differ from the amino acid sequence of amino acids 1 to 188 of SEQ ID NO: 2, 1 to 196 of SEQ ID NO: 8, 1 to 189 of SEQ ID NO: 10, and/or 1 to 188 of SEQ ID NO: 12, by an insertion or deletion of one or more amino acid residues and/or the substitution of one or more amino acid residues by different amino acid residues. In a particular embodiment, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Accordingly, for example, the invention relates to a polypeptide having, or comprising, a sequence as set forth in the mature peptide parts of either of SEQ ID NOs: 2, 8, 10, or 12, wherein conservative amino acid substitutions comprise replacements, one for another, among the basic amino acids (arginine, lysine and histidine), among the acidic amino acids (glutamic acid and aspartic acid), among the polar amino acids (glutamine and asparagine), among the hydrophobic amino acids (alanine, leucine, isoleucine, and valine), among the aromatic amino acids (phenylalanine, tryptophan and tyrosine), and among the small amino acids (glycine, alanine, serine, threonine and methionine), or any combination thereof, or active fragments thereof. Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a particular embodiment, the polypeptides of the invention and for use according to the invention are acid-stable. For the present purposes, the term acid-stable means that the residual activity after 2 hours of incubation at pH 2.0, pH 2.5 or pH 3.0 and 37° C., is at least 50%, as compared to the residual activity of a corresponding sample incubated for 2 hours at pH 9.0 and 5° C. In a particular embodiment, the residual activity is at least 60%, 70%, 80% or at least 90%. A suitable assay for determining acid-stability is the pH-stability assay of Example 2.

In another particular embodiment, the polypeptides of the invention and for use according to the invention have a relative activity at pH 7.0 of at least 0.10, 0.15, 0.20, 0.25, 0.30 or at least 0.35. The pH-profile test of Example 2 is used for the determination.

In still further particular embodiments, the polypeptides of the invention and for use according to the invention have i) a relative activity at 60° C. and pH 9 of at least 0.05, 0.10, 0.15 or at least 0.19; and/or ii) a relative activity at 70° C. of at least 0.40, 0.50, or at least 0.60. The temperature-profile test of Example 2 is used for these determinations.

The polypeptide of the invention and for use according to the invention may be a bacterial or fungal polypeptide. The fungal polypeptide may be derived from a filamentous fungus or from a yeast.

In particular embodiments, the polypeptide of the invention is i) a bacterial protease; ii) a protease of the phylum Actinobacteria; iii) of the class Actinobacteria; iv) of the order Actinomycetales v) of the family Nocardiopsaceae; vi) of the genus *Nocardiopsis*; and/or a protease derived from vii) *Nocardiopsis* species such as *Nocardiopsis alba, Nocardiopsis alkaliphila, Nocardiopsis antarctica, Nocardiopsis prasina, Nocardiopsis composta, Nocardiopsis exhalans, Nocardiopsis halophila, Nocardiopsis halotolerans, Nocardiopsis kunsanensis, Nocardiopsis listeri, Nocardiopsis lucentensis, Nocardiopsis metallicus, Nocardiopsis synnemataformans, Nocardiopsis trehalosi, Nocardiopsis tropica, Nocardiopsis umidischolae, Nocardiopsis xinjiangensis,* or *Nocardiopsis dassonvillei*, for example *Nocardiopsis dassonvillei* subsp. *dassonvillei* DSM 43235, *Nocardiopsis* sp. DSM 16424, or *Nocardiopsis alba* DSM 15647; such as a polypeptide with either of the mature amino acid sequences of SEQ ID NOs: 2, 8, 10, and 12. In a particular embodiment, the protease derives from *Nocardiopsis alba, Nocardiopsis antarctica*, or *Nocardiopsis dassonvillei*.

The above taxonomy is according to the chapter: The road map to the Manual by G. M. Garrity & J. G. Holt in Bergey's Manual of Systematic Bacteriology, 2001, second edition, volume 1, David R. Bone, Richard W. Castenholz.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, e.g. PCR, or ligating the coding sequences encoding the polypeptides so that they are in frame and that expression of the fused polypeptide is under control of the same promoter(s) and terminator.

In still further particular embodiments, the invention excludes one or more of the proteases derived from (i) *Nocardiopsis dassonvillei* NRRL 18133 which is disclosed in WO 88/03947; (ii) *Nocardiopsis* sp. strain OPC-210 (FERM P-10508) which is disclosed in JP 2-255081-A; (iii) strain ZIMET 43647 of the species *Nocardiopsis dassonvillei* which is disclosed in DD 20043218; (iv) *Nocardiopsis* sp. TOA-1 (FERM-P-18676), which is disclosed in JP 2003284571; and/or (v) the corresponding DNA.

Nucleic Acid Sequences

The present invention also relates to isolated nucleic acid sequences that encode a polypeptide of the present invention. Particular nucleic acid sequences of the invention are nucleotides 499–1062 of SEQ ID NO: 1, 577–1164 of SEQ ID NO: 7, 586–1152 of SEQ ID NO: 9, and/or 502–1065 of SEQ ID NO: 11; corresponding to the mature polypeptide encoding regions of SEQ ID NOs: 2, 8, 10, and 12, respectively. The present invention also encompasses nucleic acid sequences which encode a polypeptide having the amino acid sequence of the mature peptide parts of either of SEQ ID NOs: 2, 8, 10, and 12, but which differ from the corresponding parts of SEQ ID NOs: 1, 7, 9, and 11, respectively, by virtue of the degeneracy of the genetic code. The present invention also relates to subsequences of SEQ ID NOs: 1, 7, 9, and 11, which encode fragments of SEQ ID NOs: 2, 8, 10, and 12, respectively, which have protease activity.

A subsequence of SEQ ID NOs: 1, 7, 9, and 11, is a nucleic acid sequence encompassed by SEQ ID NOs: 1, 7, 9, and 11, respectively, except that one or more nucleotides from the 5' and/or 3' end has been deleted. Preferably, a subsequence contains at least 225 nucleotides, more preferably at least 300 nucleotides, even more preferably at least 375, 450, 500, 531, 600, 700, 800, 900 or 1000 nucleotides.

The present invention also relates to nucleotide sequences which have a degree of identity to nucleotides 499–1062 of SEQ ID NO: 1, 577–1164 of SEQ ID NO: 7, 586–1152 of SEQ ID NO: 9, and/or 502–1065 of SEQ ID NO: 11 of af least 60%. In particular embodiments, the degree of identity to either of these nucleotides is at least 62%, 64%, 66%, 68%, 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, or at least 99%.

The present invention also relates to mutant nucleic acid sequences comprising at least one mutation in the mature peptide encoding parts of either of SEQ ID NOs: 1, 7, 9, or 11, in which the mutant nucleic acid sequence encodes a polypeptide which (i) consists of the mature peptide parts of either of SEQ ID NOs: 2, 8, 10, and 12, respectively, or (ii) is a variant of any of the sequences of (i), wherein the variant comprises a substitution, deletion, and/or insertion of one or more amino acids, or (iii) is an allelic variant of any of the sequences of (i), or (iv) is a fragment of any of the sequences of (i).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Nocardiopsis* or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, allergenicity, or the like. The variant sequence may be constructed on the basis of the nucleic acid sequence presented as the polypeptide encoding part of SEQ ID NOs: 1, 7, 9 and/or 11, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the protease, or by introduction of nucleotide substitutions which may give rise to a different amino acid sequence. For a general description of nucleotide substitution, see, e.g., Ford et al., 1991, Protein Expression and Purification 2: 95–107. Low-allergenic polypeptides can e.g. be prepared as described above.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244: 1081–1085). In the latter technique, mutations are introduced at every positively charged residue in the molecule, and the resultant mutant molecules are tested for protease activity to identify amino acid residues that are critical to the activity of the molecule. Sites of substrate-protease interaction can also be determined by analysis of the three-dimensional structure as determined by such techniques as nuclear magnetic resonance analysis, crystallography or photoaffinity labelling (see, e.g., de Vos et al., 1992, Science 255: 306–312; Smith et al., 1992, Journal of Molecular Biology 224: 899–904; Wlodaver et al., 1992, FEBS Letters 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence, preferably the mature peptide encoding part, of either of SEQ ID NOs: 1, 7, 9, or 11, or their complementary strands; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 499–1062 of SEQ ID NO: 1, 577–1164 of SEQ ID NO: 7, 586–1152 of SEQ ID NO: 9, and/or 502–1065 of SEQ ID NO: 11, (ii) a subsequence of (i), or (iii) a complementary strand of (i), or (ii); and (b) isolating the nucleic acid sequence. The subsequence is preferably a sequence of at least 100 nucleotides such as a sequence that encodes a polypeptide fragment which has protease activity.

Methods for Producing Mutant Nucleic Acid Sequences

The present invention further relates to methods for producing a mutant nucleic acid sequence, comprising introducing at least one mutation into the mature polypeptide coding sequence of either of SEQ ID NOs: 1, 7, 9, or 11, or a subsequence thereof, wherein the mutant nucleic acid sequence encodes a polypeptide which consists of the mature peptides of either of SEQ ID NOs: 2, 8, 10, or 12, respectively; or a fragment thereof which has protease activity.

The introduction of a mutation into the nucleic acid sequence to exchange one nucleotide for another nucleotide may be accomplished by site-directed mutagenesis using any of the methods known in the art. Particularly useful is the procedure that utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences that direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence that directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components that are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences that mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727–3731), as well as the tac promoter (DeBoer et al., 1983, Proceedings of the National Academy of Sciences USA 80: 21–25). Further promoters are described in "Useful proteins from recombinant bacteria" in Scientific American, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

Preferred terminators for bacterial host cells, such as a *Bacillus* host cell, are the terminators from *Bacillus licheniformis* alpha-amylase gene (amyL), the *Bacillus stearothermophilus* maltogenic amylase gene (amyM), or the *Bacillus amyloliquefaciens* alpha-amylase gene (amyQ).

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred embodiment, the propeptide coding region is nucleotides 1–498 of SEQ ID NO: 1 which encode amino acids −166 to −1 of SEQ ID NO: 2, nucleotides 82–576 of SEQ ID NO: 7 which encode amino acids −165 to −1 of SEQ ID NO: 8, nucleotides 88–585 of SEQ ID NO: 9 which encode amino acids −166 to −1 of SEQ ID NO: 10, and nucleotides 1–501 of SEQ ID NO: 11 which encode amino acids −167 to −1 of SEQ ID NO: 12.

In a preferred embodiment, the signal peptide coding region is nucleotides 1–81 of SEQ ID NO: 7 which encode amino acids 1–29 of SEQ ID NO: 8, or nucleotides 1–87 of SEQ ID NO: 9 which encode amino acids 1–29 of SEQ ID NO: 10.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it functioning temperature-sensitive in the host cell (see, e.g., Ehrlich, 1978, Proceedings of the National Academy of Sciences USA 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The protease may also be co-expressed together with at least one other enzyme of interest for animal feed, such as alpha-amylase (EC 3.2.1.1), phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6).

The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease may also be expressed as a fusion protein, i.e. that the gene encoding the protease has been fused in frame to the gene encoding another protein. This protein may be another enzyme or a functional domain from another enzyme.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, or a *Streptomyces* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus*, and *Enterococcus*.

The introduction of a vector into a bacterial host cell may, for instance, be effected by protoplast transformation (see, e.g., Chang and Cohen, 1979, Molecular General Genetics 168: 111–115), using competent cells (see, e.g., Young and Spizizin, 1961, Journal of Bacteriology 81: 823–829, or Dubnau and Davidoff-Abelson, 1971, Journal of Molecular Biology 56: 209–221), electroporation (see, e.g., Shigekawa and Dower, 1988, Biotechniques 6: 742–751), or conjugation (see, e.g., Koehler and Thorne, 1987, Journal of Bacteriology 169: 5771–5278).

The host cell may be a eukaryote, such as a non-human animal cell, an insect cell, a plant cell, or a fungal cell.

In one particular embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another particular embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Examples of filamentous fungal host cells are cells of species of, but not limited to, *Acremonium, Aspergillus, Fusarium, Humicola, Mucor, Myceliophthora, Neurospora, Penicillium, Thielavia, Tolypocladium*, or *Trichoderma*.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, Proceedings of the National Academy of Sciences USA 81: 1470–1474. Suitable methods for transforming *Fusarium* species are described by Malardier et al., 1989, Gene 78: 147–156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably, the strain is of the genus *Nocardiopsis*, more preferably *Nocardiopsis dassonvillei, Nocardiopsis alba*, or *Nocardiopsis antarctica*, more preferably *Nocardiopsis dassonvillei* subsp. *dassonvillei*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence comprising at least one mutation in nucleotides 499–1062 of SEQ ID NO: 1, 577–1164 of SEQ ID NO: 7, 586–1152 of SEQ ID NO: 9, and/or 502–1065 of SEQ ID NO: 11, in which the mutant nucleic acid sequence encodes a polypeptide which (i) consists of amino acids 1 to 188 of SEQ ID NO: 2, 1 to 196 of SEQ ID NO: 8, 1 to 189 of SEQ ID NO: 10, and/or 1 to 188 of SEQ ID NO: 12, or (ii) is a variant of any of the sequences of (i), wherein the variant comprises a substitution, deletion, and/or insertion of one or more amino acids, or (iii) is an allelic variant of any of the sequences of (i), or (iv) is a fragment of any of the sequences of (i).

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a product, or disappearance of a substrate. For example, a protease assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath etal in PNAS, Feb. 15, 2000, vol. 97, no. 4, p. 1914–1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, triticale (stabilized hybrid of wheat (*Tricicum*) and rye (*Secale*), and maize (corn). Examples of dicot plants are tobacco, legumes, such as sunflower (*Helianthus*), cotton (*Gossypium*) lupins, potato, sugar beet, pea, bean and soybean, and cruciferous plants (family *Brassicaceae*), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats. Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506.

For constitutive expression, the following promoters may be used: The $^{35}$S-CaMV promoter (Franck et al., 1980, Cell 21: 285–294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675–689.; Zhang W, McElroy D. and Wu R 1991, Analysis of rice Act1 5' region activity in transgenic rice plants. Plant Cell 3, 1155–1165). Organ-specific promoters may be, for example, a promoter from storage sink tissues such as seeds, potato tubers, and fruits (Edwards & Coruzzi, 1990, Ann. Rev. Genet. 24: 275–303), or from metabolic sink tissues such as meristems (Ito et al., 1994, Plant Mol. Biol. 24: 863–878), a seed specific promoter such as the glutelin, prolamin, globulin, or albumin promoter from rice (Wu et al., 1998, Plant and Cell Physiology 39: 885–889), a *Vicia faba* promoter from the legumin B4 and the unknown seed protein gene from *Vicia faba* (Conrad et al., 1998, Journal of Plant Physiology 152: 708–711), a promoter from a seed oil body protein (Chen et al., 1998, Plant and Cell Physiology 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991–1000, the *chlorella* virus adenine methyltransferase gene promoter (Mitra and Higgins, 1994, Plant Molecular Biology 26: 85–93), or the aldP gene promoter from rice (Kagaya et al., 1995, Molecular and General Genetics 248: 668–674), or a wound inducible promoter such as the potato pin2 promoter (Xu et al., 1993, Plant Molecular Biology 22: 573–588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the protease in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15–38), and it can also be used for transforming monocots, although other transformation methods are generally preferred for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275–281; Shimamoto, 1994, Current Opinion Biotechnology 5: 158–162; Vasil et al., 1992, Bio/Technology 10: 667–674). An alternative method for transformation of monocots is based on protoplast transformation as described by Omirulleh et al., 1993, Plant Molecular Biology 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having protease activity of the present invention under conditions conducive for production of the polypeptide; and (b) recovering the polypeptide.

Animals

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having protease activity of the present invention so as to express and produce the polypeptide. The polypeptide may be recovered from the animal, e.g. from the milk of female animals, or the polypeptide may be expressed to the benefit of the animal itself, e.g. to assist the animal's digestion. Examples of animals are mentioned below in the section headed Animal Feed.

To produce a transgenic animal with a view to recovering the protease from the milk of the animal, a gene encoding the protease may be inserted into the fertilized eggs of an animal in question, e.g. by use of a transgene expression vector which comprises a suitable milk protein promoter, and the gene encoding the protease. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the protease, the transgene may be operably linked to a first regulatory sequence for salivary gland specific expression of the protease, as disclosed in WO 00/064247.

Compositions

In a still further aspect, the present invention relates to compositions comprising a polypeptide of the present invention.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptides or polypeptide compositions of the invention.

Animal Feed

The present invention is also directed to methods for using the polypeptides of the invention in animal feed, as well as to feed compositions and feed additives comprising the polypeptides of the invention.

The term animal includes all animals, including human beings. Examples of animals are non-ruminants, and ruminants. Ruminant animals include, for example, animals such as sheep, goats, horses, and cattle, e.g. beef cattle, cows, and young calves. In a particular embodiment, the animal is a non-ruminant animal. Non-ruminant animals include monogastric animals, e.g. pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may e.g. include other enzymes, in which case it could be termed a protease preparation.

The protease preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

In a particular embodiment, the protease for use according to the invention is capable of solubilising proteins. A suitable assay for determining solubilised protein is disclosed in Example 3.

The protein may be an animal protein, such as meat and bone meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

The treatment according to the invention of proteins with at least one protease of the invention results in an increased solubilisation of proteins.

The following are examples of % solubilised protein obtainable using the proteases of the invention in a monogastric in vitro model: At least 102%, 103%, 104%, 105%, 106%, or at least 107%, relative to a blank. The percentage of solubilised protein is determined using the monogastric in vitro model of Example 3 and/or Example 10. The term solubilisation of proteins basically means bringing protein(s) into solution. Such solubilisation may be due to protease-mediated release of protein from other components of the usually complex natural compositions such as feed.

In a further particular embodiment, the protease for use according to the invention is capable of increasing the amount of digestible proteins. The following are examples of % digested or digestible protein obtainable using the proteases of the invention in a monogastric in vitro model: At least 104%, 105%, 106%, 107%, 108%, 109%, 110%, 111%, 112%, 113%, 114%, 115%, or at least 116%, relative to a blank. The percentage of digested or digestible protein is determined using the in vitro model of Example 3 and/or Example 10.

The following are examples of % digested or digestible protein obtainable using the proteases of the invention in an aquaculture in vitro model: At least 103%, 104%, 105%, 106%, 107%, 108%, 109% or at least 110%, relative to a blank. The percentage of digested or digestible protein is determined using the aquaculture in vitro model of Example 4.

In a still further particular embodiment, the protease for use according to the invention is capable of increasing the Degree of Hydrolysis (DH) of proteins. The following are examples of Degree of Hydrolysis increase obtainable in a monogastric in vitro model: At least 102%, 103%, 104%, 105%, 106%, or at least 107%, relative to a blank. The DH is determined using the monogastric in vitro model of Example 3. The following are examples of Degree of Hydrolysis increase obtainable in an aquaculture in vitro model: At least 102%, 103%, 104%, 105%, 106%, or at least 107%, relative to a blank. The DH is determined using the aquaculture in vitro model of Example 4.

In a particular embodiment of a (pre-) treatment process of the invention, the protease(s) in question is affecting (or acting on, or exerting its solubilising influence on) the proteins or protein sources. To achieve this, the protein or protein source is typically suspended in a solvent, e.g. an aqueous solvent such as water, and the pH and temperature values are adjusted paying due regard to the characteristics of the enzyme in question. For example, the treatment may take place at a pH-value at which the activity of the actual protease is at least at least 40%, 50%, 60%, 70%, 80% or at least 90%. Likewise, for example, the treatment may take place at a temperature at which the activity of the actual protease is at least 40%, 50%, 60%, 70%, 80% or at least 90%. The above percentage activity indications are relative to the maximum activities. The enzymatic reaction is continued until the desired result is achieved, following which it may or may not be stopped by inactivating the enzyme, e.g. by a heat-treatment step.

In another particular embodiment of a treatment process of the invention, the protease action is sustained, meaning e.g. that the protease is added to the proteins or protein sources, but its solubilising influence is so to speak not switched on until later when desired, once suitable solubilising conditions are established, or once any enzyme inhibitors are inactivated, or whatever other means could have been applied to postpone the action of the enzyme.

In one embodiment the treatment is a pre-treatment of animal feed or proteins for use in animal feed.

The term improving the nutritional value of an animal feed means improving the availability and/or digestibility of the proteins, thereby leading to increased protein extraction from the diet components, higher protein yields, increased protein degradation and/or improved protein utilisation. The nutritional value of the feed is therefore increased, and the animal performance such as growth rate and/or weight gain and/or feed conversion ratio (i.e. the weight of ingested feed relative to weight gain) of the animal is/are improved.

In a particular embodiment the feed conversion ratio is increased by at least 1%, 2%, 3%, 4%, 5%, 6%, 7%, 8%, 9% or at least 10%. In a further particular embodiment the weight gain is increased by at least 2%, 3%, 4%, 5%, 6%, 7%, 8%, 9%, 10% or at least 11%. These figures are relative to control experiments with no protease addition.

The feed conversion ratio (FCR) and the weight gain may be calculated as described in EEC (1986): Directive de la Commission du 9 avril 1986 fixant la méthode de calcul de la valeur énergétique des aliments composes destinés à la volaille. Journal Officiel des Communautés Européennes, L130, 53–54.

The protease can be added to the feed in any form, be it as a relatively pure protease, or in admixture with other components intended for addition to animal feed, i.e. in the form of animal feed additives, such as the so-called premixes for animal feed.

In a further aspect the present invention relates to compositions for use in animal feed, such as animal feed, and animal feed additives, e.g. premixes.

Apart from the protease of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g. carotenoids such as beta-carotene, astaxanthin, and lutein; aroma compounds; stabilisers; antimicrobial peptides; polyunsaturated fatty acids; reactive oxygen generating species; and/or at least one other enzyme selected from amongst alpha-amylase (EC 3.2.1.1), phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usally fat- and water-soluble vitamins, as well as trace minerals form part of a so-called premix intended for addition to the feed, whereas macro minerals are usually separately added to the feed. A premix enriched with a protease of the invention, is an example of an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2–3. Fish diets can be characterised as indicated in column 4 of this Table B. Furthermore such fish diets usually have a crude fat content of 200–310 g/kg. WO 01/58275 corresponds to U.S. Ser. No. 09/779,334 which is hereby incorporated by reference.

An animal feed composition according to the invention has a crude protein content of 50–800 g/kg, and furthermore comprises at least one protease as claimed herein.

Furthermore, or in the alternative (to the crude protein content indicated above), the animal feed composition of the invention has a content of metabolisable energy of 10–30 MJ/kg; and/or a content of calcium of 0.1–200 g/kg; and/or a content of available phosphorus of 0.1–200 g/kg; and/or a content of methionine of 0.1–100 g/kg; and/or a content of methionine plus cysteine of 0.1–150 g/kg; and/or a content of lysine of 0.5–50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2–5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2–6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90–71463–12–5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90–72839–13–7.

In a particular embodiment, the animal feed composition of the invention contains at least one protein or protein source as defined above. It may also contain animal protein, such as Meat and Bone Meal, and/or Fish Meal, typically in an amount of 0–25%.

In still further particular embodiments, the animal feed composition of the invention contains 0–80% maize; and/or 0–80% sorghum; and/or 0–70% wheat; and/or 0–70% Barley; and/or 0–30% oats; and/or 0–40% soybean meal; and/or 0–25% fish meal; and/or 0–25% meat and bone meal; and/or 0–20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step;

and a liquid enzyme preparation is typically added after the pelleting step. The enzyme may also be incorporated in a feed additive or premix.

The final enzyme concentration in the diet is within the range of 0.01–200 mg enzyme protein per kg diet, for example in the range of 0.5–25 mg enzyme protein per kg animal diet.

The protease should of course be applied in an effective amount, i.e. in an amount adequate for improving solubilisation and/or improving nutritional value of feed. It is at present contemplated that the enzyme is administered in one or more of the following amounts (dosage ranges): 0.01–200; 0.01–100; 0.5–100; 1–50; 5–100; 10–100; 0.05–50; or 0.10–10—all these ranges being in mg protease enzyme protein per kg feed (ppm).

For determining mg enzyme protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg enzyme protein per kg feed is calculated.

The same principles apply for determining mg enzyme protein in feed additives. Of course, if a sample is available of the protease used for preparing the feed additive or the feed, the specific activity is determined from this sample (no need to purify the protease from the feed composition or the additive).

Detergent Compositions

The protease of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease of the invention. The detergent additive as well as the detergent composition may comprise one or more other enzymes such as another protease, such as alkaline proteases from *Bacillus*, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258068 and EP 305216 or from *H. insolens* as described in WO 96/13580, a *Pseudomonas* lipase, e.g. from *P. alcaligenes* or *P. pseudoalcaligenes* (EP 218272), *P. cepacia* (EP 331376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S). Suitable amylases (alpha- and/or beta-) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839. Examples of useful amylases are the variants described in WO 94/02597, WO 94/18314, WO 95/26397, WO 96/23873, WO 97/43424, WO 00/60060, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Natalase™, Supramyl™, Stainzyme™, Duramyl™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liqour, preferably 0.05–5 mg of enzyme protein per liter of wash liqour, in particular 0.1–1 mg of enzyme protein per liter of wash liqour.

The enzyme of the invention may additionally be incorporated in the detergent formulations disclosed in WO 97/07202.

Deposit of Biological Material

The following biological materials have been deposited under the terms of the Budapest Treaty with the DSMZ (Deutsche Sammlung von Mikroorganismen und Zellkulturen GmbH, Mascheroder Weg 1b, D-38124 Braunschweig, Germany), and given the following accession numbers:

| Deposit | Accession Number | Date of Deposit |
|---|---|---|
| Nocardiopsis alba | DSM 15647 | May 30, 2003 |
| Nocardiopsis sp. | DSM 16424 | May 24, 2004 |

These strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

*Nocardiopsis dassonvillei* subsp. *dassonvillei* DSM 43235 is publicly available from DSMZ. It was also deposited at other depositary institutions as follows: ATCC 23219, IMRU 1250, NCTC 10489.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Example 1

Cloning and Expression of the Protease from
*Nocardiopsis dassonvillei* subsp. *dassonvillei* DSM
43235

Reagents and Media

LB agar Described in Ausubel, F. M. et al. (eds.) "Current protocols in Molecular Biology". John Wiley and Sons, 1995

LB-PG agar LB agar supplemented with 0.5% Glucose and 0.05 M potassium phosphate, pH 7.0

PS-1 10% sucrose, 4% soybean flour, 1% $Na_3PO_4 \cdot 12H_2O$, 0.5% $CaCO_3$, and 0.01% pluronic acid TE 10 mM Tris-HCl, pH 7.4

1 mM EDTA, pH 8.0

TEL 50 mg/ml Lysozym in TE-buffer
Thiocyanate 5 M guanidium thiocyanate
100 mM EDTA
0.6% w/v N-laurylsarcosine, sodium salt
60 g thiocyanate, 20 ml 0.5 M EDTA, pH 8.0, 20 ml $H_2O$ dissolves at 65° C. Cool down to room temperature (RT) and add 0.6 g N-laurylsarcosine. Add $H_2O$ to 100 ml and filter it through a 0.2 micron sterile filter.
$NH_4Ac$ 7.5 M $CH_3COONH_4$
TER 1 microgram/ml Rnase A in TE-buffer
CIA Chloroform/isoamyl alcohol 24:1

Experimental Procedure

SEQ ID NO: 1 is the DNA sequence encoding a proform of the protease from *Nocardiopsis dassonvillei* subsp. *dassonvillei* DSM 43235. Nucleotides 499–1062 corresponds to the mature peptide encoding part.

SEQ ID NO: 2 is the deduced amino acid sequence of SEQ ID NO: 1. Amino acids −166 to −1 is the propeptide, and amino acids 1 to 188 the mature peptide.

Cloning of SEQ ID NO: 1

The wild type was grown for 3 days before harvest in the following medium at 30° C.:

| | |
|---|---|
| Trypticase | 20 g |
| Yeast extract | 5 g |
| Ferrochloride | 6 mg |
| Magnesiumsulfate | 15 mg |
| Distilled water ad | 1000 ml | pH was adjusted to 7.2 by addition of sodium hydroxide

Genomic DNA from *Nocardiopsis dassonvillei* subsp. *dassonvillei* DSM 43235 was isolated according to the following procedure:

1. Harvest 1.5 ml culture and resuspend in 100 microliters TEL. Incubate at 37° C. for 30 min.
2. Add 500 microliters thiocynate buffer and leave at room temperature for 10 min.
3. Add 250 microliters $NH_4Ac$ and leave at ice for 10 min.
4. Add 500 microliters CIA and mix.
5. Transfer to a microcentrifuge and spin for 10 min. at full speed.
6. Transfer supernatant to a new Eppendorf tube and add 0.54 volume cold isopropanol. Mix thoroughly.
7. Spin and wash the DNA pellet with 70% EtOH.
8. Resuspend the genomic DNA in 100 microliters TER.

The genomic DNA was used as template for PCR amplification using below primers SEQ ID NOS: 3 and 4. The PCR fragment was isolated on a 0.7% agarose gel and digested with restriction enzymes Cla I and BamH I. Primer 1565 (SEQ ID NO: 4) disrupts a BamH I site by changing an arginine codon from CGG to AGA and introduces a new BamH I site downstream from the stop codon.

Primers:

```
1423:
5'-GCT TTT AGT TCA TCG ATC GCA TCG (SEQ ID NO: 3)

GCT GCT CCG GCC CCC GTC CCC CAG-3'

1565:
5'-GCG GAT CCT ATT AGG TTC TGA TCC (SEQ ID NO: 4)

TGA CAC CCC AG-3'
```

The digested and purified PCR fragment was ligated to the Cla I and BamH I digested plasmid pDG268NeoMCS-PramyQ/PrcryIII/cryIIIAstab/Sav (U.S. Pat. No. 5,955,310).

The ligation mixture was used for transformation into *E. coli* TOP10F' (Invitrogen BV, The Netherlands) and several colonies were selected for miniprep (QIAprep spin, QIAGEN GmbH, Germany). The purified plasmids were checked for insert before transformation into a strain of *Bacillus subtilis* derived from *B. subtilis* DN 1885 with disrupted apr, npr and pel genes (Diderichsen et al (1990), J. Bacteriol., 172, 4315–4321). The disruption was performed essentially as described in "*Bacillus subtilis* and other Gram-Positive Bacteria," American Society for Microbiology, p.618, eds. A. L. Sonenshein, J. A. Hoch and Richard Losick (1993). Transformed cells were plated on 1% skim milk LB-PG agar plates, supplemented with 6 μg/ml chloramphenicol. The plated cells were incubated over night at 37° C. and protease containing colonies were identified by a surrounding clearing zone. Protease positive colonies were selected and the coding sequence of the expressed enzyme from the expression construct was confirmed by DNA sequence analysis.

Fermentation

The *Bacillus subtilis* host cell transformed as described above was fermented on a rotary shaking table (250 r.p.m.) in 500 ml baffled Erlenmeyer flasks containing 100 ml PS-1 medium supplemented with 6 μg/ml chloramphenicol, at 37° C. for 16 hours and at 26° C. for extra 4 days.

Example 2

Purification and Characterization of the Protease from *Nocardiopsis dassonvillei* subsp. *dassonvillei* DSM 43235

Protease Assays 1) pNA Assay:

pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0, 11.0, and 12.0 with HCl or NaOH.

20 microliters protease (diluted in 0.01% Triton X-100) is mixed with 100 microliters assay buffer. The assay is started by adding 100 microliters pNA substrate (50 mg dissolved in 1.0 ml DMSO and further diluted 45× with 0.01% Triton X-100). The increase in $OD_{405}$ is monitored as a measure of the protease activity.

2) Protazyme AK Assay:

Substrate: Protazyme AK tablet (cross-linked and dyed casein; from Megazyme)
Temperature: controlled (assay temperature).
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.

A Protazyme AK tablet is suspended in 2.0 ml 0.01% Triton X-100 by gentle stirring. 500 microliters of this suspension and 500 microliters assay buffer are mixed in an Eppendorf tube and placed on ice. 20 microliters protease sample (diluted in 0.01% Triton X-100) is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200 microliters supernatant is transferred to a microtiter plate. $OD_{650}$ is read as a measure of protease activity. A buffer blind is included in the assay (instead of enzyme).

Experimental Procedure

The protease fermentation described in Example 1 was centrifuged (20000×g, 20 min) and the supernatants were carefully decanted from the precipitates. The combined supernatants were filtered through a Seitz EKS plate in order to remove the rest of the *Bacillus* host cells. The EKS filtrate was transferred to 50 mM $H_3BO_3$, 5 mM succinic acid, 1 mM $CaCl_2$, pH 7 on a G25 sephadex column and applied to a bacitracin silica column equilibrated in the same buffer. After washing the column extensively with the equilibration buffer, the protease was step-eluted with 100 mM $H_3BO_3$, 10 mM succinic acid, 2 mM $CaCl_2$, 1 M NaCl, 25% isopropanol, pH 7. The bacitracin eluate was transferred to 50 mM $H_3BO_3$, 10 mM $CH_3COOH$, 1 mM $CaCl_2$, pH 4.5 and applied to a S sepharose HP column equilibrated in the same buffer. After washing the column extensively with the equilibration buffer, the protease was eluted with a linear NaCl gradient (0→0.5 M) in the same buffer. Fractions from the column were analysed for protease activity (using the Protazyme AK assay at 37° C. and pH 9) and active fractions were further analysed by SDS-PAGE. Fractions, where only one band was seen on the coomassie stained SDS-PAGE gel, were pooled as the purified preparation and was used for further characterization.

pH-Activity, pH-Stability, and Temperature-Activity

The pNA assay was used for obtaining the pH-activity profile as well as the pH-stability profile. For the pH-stability profile the protease was diluted 10× in the assay buffers and incubated for 2 hours at 37° C. After incubation the protease samples were transferred to the same pH-pH 9, before assay for residual activity, by dilution in the pH 9 assay buffer. The Protazyme AK assay was used for obtaining the temperature-activity profile at pH 9. The results are shown in Tables 1–3 below.

TABLE 1 pH-activity profile

| pH | Protease derived from *Nocardiopsis dassonvillei* subsp. *dassonvillei* DSM 43235 | Protase derived from *Nocardiopsis* sp. NRRL 18262 |
| --- | --- | --- |
| 2 | 0.00 | — |
| 3 | 0.00 | 0.00 |
| 4 | 0.03 | 0.02 |
| 5 | 0.11 | 0.07 |
| 6 | 0.21 | 0.21 |
| 7 | 0.37 | 0.44 |
| 8 | 0.71 | 0.67 |
| 9 | 0.97 | 0.88 |
| 10 | 1.00 | 1.00 |
| 11 | 0.94 | 0.93 |

TABLE 2 pH-stability profile

| pH | Protease derived from *Nocardiopsis dassonvillei* subsp. *dassonvillei* DSM 43235 | Protase derived from *Nocardiopsis* sp. NRRL 18262 |
| --- | --- | --- |
| 2.0 | 1.00 | 0.78 |
| 2.5 | 0.95 | 1.00 |
| 3.0 | 0.97 | 1.03 |
| 3.5 | 1.01 | 0.98 |
| 4.0 | 0.98 | 0.99 |
| 5.0 | 0.97 | 1.02 |
| 6.0 | 0.98 | 1.00 |
| 7.0 | 0.96 | 1.01 |
| 8.0 | 0.99 | 0.98 |
| 9.0 | 0.99 | 0.99 |
| 10.0 | 0.96 | 0.99 |
| 11.0 | 0.94 | 0.86 |
| 12.0 | 0.84 | — |
| 9.0 and after 2 hours at 5° C. | 1.00 | 1.00 |

TABLE 3

Temperature activity profile

| Temperature (° C.) | Protease derived from *Nocardiopsis dassonvillei* subsp. *dassonvillei* DSM 43235 | Protase derived from *Nocardiopsis* sp. NRRL 18262 |
| --- | --- | --- |
| 15 | 0.08 | 0.02 |
| 25 | 0.01 | 0.02 |
| 37 | 0.03 | 0.07 |
| 50 | 0.09 | 0.20 |
| 60 | 0.19 | 0.51 |
| 70 | 0.63 | 1.00 |
| 80 | 1.00 | 0.39 |
| 90 | 0.35 | — |

Differential Scanning Calorimetry (DSC)

DSC was used to determine temperature stability at pH 7.0 of the proteases derived from *Nocardiopsis dassonvillei* subsp. *dassonvillei* DSM 43235 and from *Nocardiopsis* sp. NRRL 18262. Purified proteases were dialysed over night at 4° C. against 10 mM sodium phosphate, 50 mM sodium chloride, pH 7.0 and run on a VP-DSC instrument (Micro Cal) with a constant scan rate of 1.5° C./min from 20 to 100° C. Data-handling was performed using the MicroCal Origin software.

The resulting denaturation or melting temperatures, $T_m$'s, were: For the protease of the invention derived from *Nocardiopsis dassonvillei* subsp. *dassonvillei*: 83.0° C.; for the protease derived from *Nocardiopsis* sp. NRRL 18262: 76.5° C.

Other Characteristics

The protease was found to be inhibited by Phenyl Methyl Sulfonyl Fluoride. Its relative molecular weight as determined by SDS-PAGE was $M_r$=20 kDa, and the N-terminal sequence: ADIIGGLAYYMGGRC.

Example 3

Performance of the *Nocardiopsis dassonvillei* subspecies *dassonvillei* DSM 43235 Protease in a Monogastric In Vitro Digestion Model The performance of a purified preparation of the mature part of the protease having SEQ ID NO: 2 (prepared as described in Examples 1 and 2) was tested in an in vitro model simulating the digestion in monogastric animals. In particular, the protease was tested for its ability to improve solubilisation and digestion of maize/-SBM (maize/-soybean meal) proteins. In the tables below, this protease is designated "protease of the invention." The in vitro system consisted of 15 flasks in which maize/-SBM substrate was initially incubated with HCl/pepsin—simulating gastric digestion—and subsequently with pancreatin—simulating intestinal digestion. 10 of the flasks were dosed with the protease at the start of the gastric phase whereas the remaining flasks served as blanks. At the end of the intestinal incubation phase samples of in vitro digesta were removed and analysed for solubilised and digested protein.

Outline of In Vitro Digestion Procedure

| Components added | pH | Temperature | Time course | Simulated digestion phase |
| --- | --- | --- | --- | --- |
| 10 g maize/-SBM substrate (6:4), 41 ml HCl (0.105 M) | 3.0 | 40° C. | t = 0 min | Mixing |
| 5 ml HCl (0.105 M)/pepsin (3000 U/g substrate), 1 mL protease of the invention | 3.0 | 40° C. | t = 30 min | Gastric digestion |
| 16 ml H$_2$O | 3.0 | 40° C. | t = 1.0 hour | Gastric digestion |
| 7 ml NaOH (0.39 M) | 6.8 | 40° C. | t = 1.5 hours | Intestinal digestion |
| 5 ml NaHCO$_3$ (1 M)/ pancreatin (8 mg/g diet) | 6.8 | 40° C. | t = 2.0 hours | Intestinal digestion |
| Terminate incubation | 7.0 | 40° C. | t = 6.0 hours | |

Conditions
Substrate: 4 g SBM, 6 g maize (premixed)
pH: 3.0 stomach step/6.8–7.0 intestinal step
HCl: 0.105 M for 1.5 hours (i.e. 30 min HCl-substrate premixing)
pepsin: 3000 U/g diet for 1 hour
pancreatin: 8 mg/g diet for 4 hours
temperature: 40° C.

Replicates: 5

Solutions
0.39 M NaOH
0.105 M HCl
0.105 M HCl containing 6000 U pepsin per 5 ml
1 M NaHCO$_3$ containing 16 mg pancreatin per ml
125 mM NaAc-buffer, pH 6.0

Enzyme Protein Determinations

The amount of protease enzyme protein (in what follows, Enzyme Protein is abbreviated EP) is calculated on the basis of the A$_{280}$ values and the amino acid sequences (amino acid compositions) using the principles outlined in S. C. Gill & P. H. von Hippel, Analytical Biochemistry 182, 319–326 (1989).

Experimental Procedure for In Vitro Model

The experimental procedure was according to the above outline. pH was measured at time 1, 2.5, and 5.5 hours. Incubations were terminated after 6 hours and samples of 30 ml were removed and placed on ice before centrifugation (10000×g, 10 min, 4° C.). Supernatants were removed and stored at −20° C.

Analysis

All samples were analysed for % degree of protein with the OPA method as well as content of solubilised and digested protein using gel filtration.

DH Determination by the OPA-Method

The Degree of Hydrolysis (DH) of protein in different samples was determined using an semi-automated microtiter plate based calorimetric method (Nielsen, P. M.; Petersen, D.; Dambmann, C. Improved method for determining food protein degree of hydrolysis. J. Food Sci. 2001, 66, 642–646). The OPA reagent was prepared as follows: 7.620 g di-Na tetraborate decahydrate and 200 mg sodiumdodecyl sulphate (SDS) were dissolved in 150 ml deionized water. The reagents were completely dissolved before continuing. 160 mg o-phthal-dialdehyde 97% (OPA) was dissolved in 4 ml ethanol. The OPA solution was transferred quantitatively to the above-mentioned solution by rinsing with deionized water. 176 mg dithiothreitol 99% (DTT) was added to the solution that was made up to 200 ml with deionized water. A serine standard (0.9516 meqv/l) was prepared by solubilising 50 mg serine (Merck, Germany) in 500 ml deionized water.

The sample solution was prepared by diluting each sample to an absorbance (280 nm) of about 0.5. Generally, supernatants were diluted (100×) using an automated Tecan dilution station (Männedorf, Switzerland). All other spectrophotometer readings were performed at 340 nm using deionized water as the control. 25 microliters of sample, standard and blind was dispensed into a microtiter plate. The micro-titer plate was inserted into an iEMS MF reader (Labsystems, Finland) and 200 microliters of OPA reagent was automatically dispensed. Plates were shaken (2 min; 700 rpm) before measuring absorbance. Finally, the DH was calculated. Eightfold determination of all samples was carried out.

Estimation of Solubilised and Digested Protein

The content of solubilised protein in supernatants from in vitro digested samples was estimated by quantifying crude protein (CP) using gel filtration HPLC. Supernatants were thawed, filtered through 0.45 μm polycarbonate filters and diluted (1:50, v/v) with H$_2$O. Diluted samples were chromatographed by HPLC using a Superdex Peptide PE (7.5× 300 mm) gel filtration column (Global). The eluent used for isocratic elution was 50 mM sodium phosphate buffer (pH 7.0) containing 150 mM NaCl. The total volume of eluent per run was 26 ml and the flow rate was 0.4 ml/min. Elution profiles were recorded at 214 nm and the total area under the profiles was determined by integration. To estimate protein content from integrated areas, a calibration curve (R$^2$=0.9993) was made from a dilution series of an in vitro digested reference maize/-SBM sample with known total protein content. The protein determination in this reference sample was carried out using the Kjeldahl method (determination of % nitrogen; A.O.A.C. (1984) Official Methods of Analysis 14th ed., Washington D.C.).

The content of digested protein was estimated by integrating the chromatogram area corresponding to peptides and amino acids having a molecular mass of 1500 Dalton or below (Savoie, L.; Gauthier, S. F. Dialysis Cell For The In-vitro Measurement Of Protein Digestibility. J. Food Sci. 1986, 51, 494–498; Babinszky, L.; Van, D. M. J. M.; Boer, H.; Den, H. L. A. An In-vitro Method for Prediction of The Digestible Crude Protein Content in Pig Feeds. J. Sci. Food Agr. 1990, 50, 173–178; Boisen, S.; Eggum, B. O. Critical Evaluation of In-vitro Methods for Estimating Digestibility in Simple-Stomach Animals. Nutrition Research Reviews 1991, 4, 141–162). To determine the 1500 Dalton dividing line, the gel filtration column was calibrated using cytochrome C (Boehringer, Germany), aprotinin, gastrin 1, and substance P (Sigma Aldrich, USA), as molecular mass standards.

Results

The results shown in Tables 4 and 5 below indicate that the protease increased the Degree of Hydrolysis (DH), as well as soluble and digestible protein significantly.

TABLE 4

Degree of Hydrolysis (DH), absolute and relative values

| Enzyme (dosage in mg EP/kg feed) | n | Of total protein | | Relative to blank | |
|---|---|---|---|---|---|
| | | % DH | SD | % DH | % CV |
| Blank | 5 | 26.84 [a] | 0.69 | 100.0 [a] | 2.57 |
| Protease of the invention (100) | 5 | 28.21 [b] | 0.35 | 105.1 [b] | 1.25 |

Different letters within the same column indicate significant differences (1-way ANOVA, Tukey-Kramer test, $P < 0.05$).
SD = Standard Deviation.
% CV = Coefficient of Variance = (SD/mean value) × 100%

TABLE 5

Solubilised and digested crude protein measured by ÄKTA HPLC.

| Enzyme (dosage in mg EP/kg feed) | n | Of total protein | | | | Relative to blank | | | |
|---|---|---|---|---|---|---|---|---|---|
| | | % dig. CP | SD | % sol. CP | SD | % dig. CP | CV % | % sol. CP | CV % |
| Blank | 5 | 54.1 [a] | 1.1 | 90.1 [a] | 1.1 | 100.0 [a] | 2.0 | 100.0 [a] | 1.2 |
| Protease of the invention (50) | 5 | 57.7 [b] | 1.1 | 93.2 [b] | 1.4 | 106.7 [b] | 1.9 | 103.4 [b] | 1.5 |
| (100) | 5 | 58.9 [b] | 0.8 | 94.8 [b] | 0.9 | 108.9 [b] | 1.3 | 105.2 [b] | 0.9 |

Different letters within the same column indicate significant differences (1-way ANOVA, Tukey-Kramer test, $P < 0.05$).
SD = Standard Deviation.
% CV = Coefficient of Variance = (SD/mean value) × 100%

Example 4

Performance of the Protease from *Nocardiopsis dassonvillei* subsp. *dassonvillei* DSM 43235 in an Aquaculture In Vitro Model The protease preparation as described in Example 3 was tested in an aquaculture in vitro model simulating the digestion in coldwater fish. The in vitro system consisted of 15 flasks in which SBM substrate was initially incubated with HCl/pepsin—simulating gastric digestion—and subsequently with pancreatin—simulating intestinal digestion. 10 of the flasks were dosed with the protease at the start of the gastric phase whereas the remaining 5 flasks served as blanks. At the end of the intestinal incubation phase samples of in vitro digesta were removed and analysed for solubilised and digested protein.

Outline of Aqua In Vitro Digestion Procedure

| Components added | pH | Temperature | Time course | Simulated digestion phase |
|---|---|---|---|---|
| 10 g extruded SBM substrate, 62 ml HCl (0.155 M)/pepsin (4000 U/g substrate), 1 mL of the protease of the invention | 3.0 | 15° C. | T = 0 min | Gastric digestion |
| 7 mL NaOH (1.1 M) | 6.8 | 15° C. | t = 6 hours | Intestinal digestion |
| 5 mL NaHCO$_3$ (1 M)/pancreatin (8 mg/g diet) | 6.8 | 15° C. | t = 7 hours | Intestinal digestion |
| Terminate incubation | 7.0 | 15° C. | t = 24 hours | |

Conditions
Substrate: 10 g extruded SBM
pH: 3.0 stomach step/6.8–7.0 intestinal step
HCl: 0.155 M for 6 hours
Pepsin: 4000 U/g diet for 6 hours
Pancreatin: 8 mg/g diet for 17 hours
Temperature: 15° C.
Replicates: 5

Solutions
1.1 M NaOH
0.155 M HCl/pepsin (4000 U/g diet)
1 M NaHCO$_3$containing 16 mg pancreatin/mL
125 mM NaAc-buffer, pH 6.0

Experimental Procedure for Aqua In Vitro Model

The experimental produce was according to the above outline. pH was measured at time 1, 5, 8 and 23 hours. Incubations were terminated after 24 hours and samples of 30 mL were removed and placed on ice before centrifugation (13000×g, 10 min, 0° C.). Supernatants were removed and stored at −20° C.

Analysis

All supernatants were analysed using the OPA method (% degree of hydrolysis) and by ÄKTA HPLC to determine solubilised and digested protein (see monogastric example).

Pre-Treatment of In Vitro Supernatants with EASY SPE Columns

Before analysis on ÄKTA HPLC supernatants from the in vitro system were pretreated using solid-phase sample purification. This was done to improve the chromatography and thereby prevent unstable elution profiles and baselines. The columns used for extraction were solid phase extraction columns (Chromabond EASY SPE Columns from Macherey-Nagel). 2 mL milliQ water was eluted through the columns by use of a vacuum chamber (vacuum 0.15×100 kPa). Subsequently 3 mL in vitro sample was dispensed onto the column and eluted (vacuum 0.1×100 kPa), the first ½ mL of eluted sample was thrown away and a clean tube was placed beneath the column, then the rest of the sample was eluted and saved for further dilution.

Results

The results shown in Tables 6 and 7 below indicate that the protease significantly increased Degree of hydrolysis and protein digestibility.

TABLE 6

| Enzyme | Degree of Hydrolysis (DH) | | | | |
|---|---|---|---|---|---|
| | | Of total protein | | Relative to blank | |
| (mg EP/kg diet) | n | % DH | SD | % DH | % CV |
| Blank | 5 | 21.30 [a] | 0.52 | 100.0 [a] | 2.42 |
| Protease of the invention (50) | 5 | 21.98 [b] | 0.22 | 103.2 [b] | 1.00 |

Different letters within the same column indicate significant differences (1-way ANOVA, Tukey-Kramer test, P < 0.05).
SD = Standard Deviation.
% CV = Coefficient of Variance = (SD/mean value) × 100%

TABLE 7

| Enzyme (mg EP/kg diet) | Solubilised and digested crude protein | | | | | | | |
|---|---|---|---|---|---|---|---|---|
| | | Of total protein | | | | Relative to blank | | |
| | n | % CP dig | SD | % CP sol | SD | % CP dig | % CV | % CP sol | CV % |
| Blank | 5 | 50.0 [a] | 2.2 | 89.9 [a] | 3.2 | 100.0 [a] | 4.5 | 100.0 [a] | 3.5 |
| Protease of the invention (50) | 5 | 52.3 [b] | 1.1 | 91.4 [a] | 1.5 | 104.8 [b] | 2.1 | 101.7 [a] | 1.6 |
| (100) | 5 | 53.4 [b] | 0.4 | 91.6 [a] | 1.0 | 107.0 [b] | 0.7 | 101.9 [a] | 1.1 |

Different letters within the same column indicate significant differences (1-way ANOVA, Tukey-Kramer test, P < 0.05).
SD = Standard Deviation.
% CV = Coefficient of Variance = (SD/mean value) × 100%.

Example 5

Construction of *Bacillus subtilis* Strains L2, L2 HV0 and L2 HV1

Two "Tail" variants (having C-terminal extensions) of the protease having the amino acid sequence of amino acids 1–188 of SEQ ID NO: 2 were also made. The tail variant designated hereinafter L2 HV0 had the following 8 amino acids extra in the C-terminus: QSHVQSAP with the following DNA sequence extension inserted in front of the TAA stopcodon (between nucleotides 1059 and 1060 of SEQ ID NO: 1):

5'-CAATCGCATGTTCAATCCGCTCCA-3'    (SEQ ID NO: 5)

The tail variant designated L2 HV1 had the following 4 amino acids extra in the C-terminus: QSAP, with the following DNA sequence extension inserted in front of the TAA stopcodon (between nucleotides 1059 and 1060 of SEQ ID NO: 1):

5'-CAATCGGCTCCT-3'    (SEQ ID NO: 6)

Three strains of *Bacillus subtilis* were constructed: One harbouring the DNA construct encoding the protease having the amino acid sequence of amino acids 1–188 of SEQ ID NO: 2, denoted L2, and two harbouring the DNA constructs encoding the tail variants L2 HV0, and L2 HV1, respectively. These constructs were fused by PCR to the DNA coding for the signal peptide from SAVINASE™ *Bacillus clausii* (Takami, H.; Kobayashi, T.; Kobayashi, M.; Yamamoto, M.; Nakamura, S.; Aono, R.; Horikoshi, K.; Molecular cloning, nucleotide sequence and expression of the structural gene for alkaline protease from alkaliphilic *Bacillus* sp. 221) Biosci. Biotechnol. Biochem. 56:1455 (1992) and integrated by homologous recombination on the *Bacillus subtilis* host cell genome (described in Example 1). The genes are expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as marker.

(Described in e.g. Diderichsen, B.; Poulsen, G. B.; Joergensen, S. T.; A useful cloning vector for *Bacillus subtilis*. Plasmid 30:312 (1993)).

Chloramphenicol resistance transformants were checked for protease activity on 1% skim milk LB-PG agar plates (supplemented with 6 micrograms/ml chloramphenicol). Some protease positive colonies were further analyzed by DNA sequencing of the insert for correct gene DNA sequence and a strain of each construct was selected, called strain *B. subtilis* L2, *B. subtilis* L2 HV0, *B. subtilis* L2 HV1.

Example 6

Fermentation of the *B. subtilis* Strains L2, L2 HV0 and L2 HV1

The three *B. subtilis* strains L2, L2 HV0 and L2 HV1, were fermented on a rotary shaking table in 500 ml baffled Erlenmeyer flasks containing 100 ml TY supplemented with 6 mg/l chlorampinicol.

Six Erlenmeyer flasks for each of the three *B. subtilis* strains were fermented in parallel. Two of the six Erlenmeyer flasks were incubated at 37° C. (250 rpm), two at 30° C. (250 rpm), and the last two at 26° C. (250 rpm).

A sample was taken from each shake flask at day 1, 2 and 3 and analyzed for proteolytic activity.

TABLE 8

Proteolytic activity at 37° C.

| Strain | Relative values at 37° C. | | |
|---|---|---|---|
| | Day 1 | Day 2 | Day 3 |
| L2 | 1.0 | 1.0 | 1.0 |
| L2-HV1 | 1.4 | 1.3 | 1.2 |
| L2-HV0 | 1.3 | 1.1 | 1.4 |

TABLE 9

Proteolytic activity at 30° C.

| Strain | Relative values at 30° C. | | |
|---|---|---|---|
| | Day 1 | Day 2 | Day 3 |
| L2 | 1.0 | 1.0 | 1.0 |
| L2-HV1 | 1.0 | 1.2 | 1.4 |
| L2-HV0 | 1.1 | 1.3 | 1.3 |

TABLE 10

Proteolytic activity at 26° C.

| Strain | Relative values at 26° C. | | |
|---|---|---|---|
| | Day 1 | Day 2 | Day 3 |
| L2 | 1.0 | 1.0 | 1.0 |
| L2-HV1 | 1.3 | 1.1 | 1.1 |
| L2-HV0 | 0.2 | 1.1 | 1.1 |

As it can be seen from Tables 8–10 above the effect of the tails increases the expression level for the S2A protease from *Nocardiopsis dassonvillei* subsp. *dassonvillei*, DSM 43235 when expressed in *B. subtilis*. An increase of up to 40% is observed in this experiment, but overall an improvement is observed for both tail variants, L2 HV1 and L2 HV0, at all three temperatures tested.

Example 7

Protease 22

A protease designated "Protease 22" was designed so as to comprise the following characteristic amino acids of the mature part (amino acids 1–188) of SEQ ID NO: 2: 10Y, 38T, 82S, 95P, 99A, 100V, 114I, 118N, 120T, 122R, 125Q, 129Y, 130S, 131L, 165S, and 171Y; wherein each position corresponds to a position of SEQ ID NO: 2.

The mature part of Protease 22 is amino acids 1–196 of SEQ ID NO: 8. The DNA sequence corresponding to SEQ ID NO: 8 is SEQ ID NO: 7.

The DNA sequence of SEQ ID NO: 7 was constructed and introduced into a *Bacillus* host for expression. The expressed protease was purified and characterized as an alpha-lytic protease (peptidase family S1E and/or S2A).

The temperature-activity relationship of Protease 22 was measured at pH9, using the Protazyme AK assay of Example 2. For comparison purposes the protease from *Nocardiopsis* sp. NRRL 18262 was included. The results are shown in Table 11 below.

The denaturation or melting temperature of Protease 22 was determined as described in Example 2 to $T_m$=83.5° C.

TABLE 11

Temperature profiles

| | Relative activity at pH 9 | |
|---|---|---|
| Temperature (° C.) | Protease 22 | Protease from *Nocardiopsis* sp. NRRL 18262 |
| 15 | 0.016 | 0.015 |
| 25 | 0.010 | 0.024 |
| 37 | 0.028 | 0.068 |
| 50 | 0.069 | 0.199 |
| 60 | 0.138 | 0.510 |
| 70 | 0.474 | 1.000 |
| 80 | 1.000 | 0.394 |
| 90 | 0.375 | — |

From these results it appears that Protease 22 has a higher melting temperature, and a higher temperature optimum at pH 9, both as compared to the *Nocardiopsis* sp. NRRL 18262 protease, viz. a melting temperature increase of 7.0° C., and a temperature optimum increase of around 10° C.

Example 8

Protease L2a

The mature part of protease L2a is amino acids 1–189 of SEQ ID NO: 10. SEQ ID NO: 9 is the DNA sequence corresponding to SEQ ID NO: 10.

The DNA sequence of SEQ ID NO: 9 was constructed and introduced into a *Bacillus* host for expression as described in Example 1, and purified as described in Example 2.

Protease L2a is an alpha-lytic protease (peptidase family S1E and/or S2A).

The temperature-activity relationship of protease L2a was measured at pH 9, using the Protazyme AK assay of Example 2. For comparison purposes the protease from *Nocardiopsis* sp. NRRL 18262 (Protease 10) was included. The results are shown in Table 12 below.

The denaturation or melting temperature of the L2a protease was determined as described in Example 2 to $T_m$=78.2° C.

TABLE 12

Temperature activity profile

| Temperature (° C.) | L2a protease | Protease 10 |
|---|---|---|
| 15 | 0.02 | 0.02 |
| 25 | 0.02 | 0.02 |
| 37 | 0.05 | 0.07 |
| 50 | 0.13 | 0.20 |
| 60 | 0.31 | 0.51 |
| 70 | 0.79 | 1.00 |
| 80 | 1.00 | 0.39 |
| 90 | 0.28 | — |

From these results it appears that protease L2a has a higher melting temperature, and a higher temperature optimum at pH 9, both as compared to the *Nocardiopsis* sp. NRRL 18262 protease, viz. a melting temperature increase of 1.7° C., and a temperature optimum increase of around 10° C.

Example 9

Protease 8

The mature part of protease 8 is amino acids 1–188 of SEQ ID NO: 12. SEQ ID NO: 11 is the DNA sequence corresponding to SEQ ID NO: 12.

The DNA sequence of SEQ ID NO: 11 was constructed and introduced into a *Bacillus* host for expression as described in Example 1, and purified as described in Example 2.

Protease 8 is an alpha-lytic protease (peptidase family S1E and/or S2A).

The temperature-activity relationship of Protease 8 was measured at pH9, using the Protazyme AK assay of Example 2. For comparison purposes the protease from *Nocardiopsis* sp. NRRL 18262 (Protease 10) was included. The results are shown in Table 13 below.

The denaturation or melting temperature of Protease 8 was determined as described in Example 2 to $T_m$=78.3° C.

TABLE 13

Temperature activity profile

| Temperature (° C.) | Protease 8 | Protease 10 |
|---|---|---|
| 15 | 0.02 | 0.02 |
| 25 | 0.05 | 0.02 |
| 37 | 0.10 | 0.07 |
| 50 | 0.27 | 0.20 |
| 60 | 0.56 | 0.51 |
| 70 | 1.00 | 1.00 |
| 80 | 0.49 | 0.39 |
| 90 | — | — |

From these results it appears that Protease 8 has a higher melting temperature, and a higher temperature optimum at pH 9, both as compared to Protease 10, e.g. a melting temperature increase of 1.8° C.

Example 10

Performance of the L2a Protease in a Monogastric In Vitro Digestion Model

The performance of the purified L2a protease described in Example 8 was tested in an in vitro model simulating the digestion in monogastric animals, in comparison with the known protease derived from *Nocardiopsis* sp. NRRL 18262 ("Protease 10"). In particular, the protease was tested for its ability to improve solubilisation and digestion of maize/-SBM (maize/-soybean meal) proteins. The in vitro system consisted of 18 flasks in which maize/-SBM substrate was initially incubated with HCl/pepsin—simulating gastric digestion—and subsequently with pancreatin—simulating intestinal digestion. Eight of the flasks were dosed with the protease at the start of the gastric phase whereas the remaining ten flasks served as blanks. At the end of the intestinal incubation phase samples of in vitro digesta were removed and analysed for solubilised and digested protein.

Outline of In Vitro Digestion Procedure

| Components added | pH | Temperature | Time course | Simulated digestion phase |
|---|---|---|---|---|
| 10 g maize/-SBM substrate (6:4), 41 ml HCl (0.105 M) | 3.0 | 40° C. | t = 0 min | Mixing |
| 5 ml HCl (0.105 M)/pepsin (3000 U/g substrate), 1 ml protease (to provide 100 mg protease enzyme protein per kg of substrate) | 3.0 | 40° C. | t = 30 min | Gastric digestion |
| 16 ml H$_2$O | 3.0 | 40° C. | t = 1.0 hour | Gastric digestion |
| 7 ml NaOH (0.39 M) | 6.8 | 40° C. | t = 1.5 hours | Intestinal digestion |
| 5 ml NaHCO$_3$ (1 M)/ pancreatin (8 mg/g diet) | 6.8 | 40° C. | t = 2.0 hours | Intestinal digestion |
| Terminate incubation | 7.0 | 40° C. | t = 6.0 hours | |

Conditions

Substrate: 4 g SBM, 6 g maize (premixed)
pH: 3.0 stomach step/6.8–7.0 intestinal step
HCl: 0.105 M for 1.5 hours (i.e. 30 min HCl-substrate premixing)
pepsin: 3000 U/g diet for 1 hour
pancreatin: 8 mg/g diet for 4 hours
temperature: 40° C.
Replicates: n Solutions 0.39 M NaOH
0.105 M HCl
0.105 M HCl containing 6000 U pepsin per 5 ml
1 M NaHCO$_3$ containing 16 mg pancreatin per ml
125 mM NaAc-buffer, pH 6.0

Enzyme Protein Determinations

The amount of protease enzyme protein (EP) is calculated on the basis of the A$_{280}$ values and the amino acid sequences (amino acid compositions) using the principles outlined in S. C. Gill & P. H. von Hippel, Analytical Biochemistry 182, 319–326 (1989).

Experimental Procedure for In Vitro Model

The experimental procedure was according to the above outline. pH was measured at time 1, 2.5, and 5.5 hours. Incubations were terminated after 6 hours and samples of 30 ml were removed and placed on ice before centrifugation (10000×g, 10 min, 4° C.). Supernatants were removed and stored at 20° C.

Analysis

All samples were analysed for content of solubilised and digested protein using gel filtration.

Estimation of Solubilised and Digested Protein

The content of solubilised protein in supernatants from in vitro digested samples was estimated by quantifying crude protein (CP) using gel filtration HPLC. Supernatants were thawed, filtered through 0.45 μm polycarbonate filters and diluted (1:50, v/v) with $H_2O$. Diluted samples were chromatographed by HPLC using a Superdex Peptide PE (7.5× 300 mm) gel filtration column (Global). The eluent used for isocratic elution was 50 mM sodium phosphate buffer (pH 7.0) containing 150 mM NaCl. The total volume of eluent per run was 26 ml and the flow rate was 0.4 ml/min. Elution profiles were recorded at 214 nm and the total area under the profiles was determined by integration. To estimate protein content from integrated areas, a calibration curve ($R^2$=0.9993) was made from a dilution series of an in vitro digested reference maize/-SBM sample with known total protein content. The protein determination in this reference sample was carried out using the Kjeldahl method (determination of % nitrogen; A.O.A.C. (1984) Official Methods of Analysis 14th ed., Washington D.C.).

The content of digested protein was estimated by integrating the chromatogram area corresponding to peptides and amino acids having a molecular mass of 1500 Dalton or below (Savoie, L.; Gauthier, S. F. Dialysis Cell For The In-vitro Measurement Of Protein Digestibility. J. Food Sci. 1986, 51, 494–498; Babinszky, L.; Van, D. M. J. M.; Boer, H.; Den, H. L. A. An In-vitro Method for Prediction of The Digestible Crude Protein Content in Pig Feeds. J. Sci. Food Agr. 1990, 50, 173–178; Boisen, S.; Eggum, B. O. Critical Evaluation of In-vitro Methods for Estimating Digestibility in Simple-Stomach Animals. Nutrition Research Reviews 1991, 4, 141–162). To determine the 1500 Dalton dividing line, the gel filtration column was calibrated using cytochrome C (Boehringer, Germany), aprotinin, gastrin 1, and substance P (Sigma Aldrich, USA), as molecular mass standards.

Results

The results shown in Table 14 below indicate that the L2a protease, like Protease 10, significantly increased the level of soluble and digestible protein relative to the blank. Furthermore, the L2a protease appears to at least numerically improve the level of digestible protein as compared to the known Protease 10.

TABLE 14

| Solubilised and digested crude protein | | | | | |
|---|---|---|---|---|---|
| | | Relative to blank | | | |
| Enzyme | n | % digestible CP | CV % | % soluble CP | CV % |
| Blank | 10 | 100.0 a | 5.5 | 100.0 a | 4.4 |
| L2a protease | 3 | 116.1 b | 0.7 | 107.2 b | 1.1 |
| Protease 10 | 5 | 112.1 b | 1.0 | 110.2 b | 0.6 |

Different letters within the same column indicate significant differences (1-way ANOVA, Tukey-Kramer test, P < 0.05).
SD = Standard Deviation.
% CV = Coefficient of Variance = (SD/mean value) × 100%

Example 11

Fish Feeding Trial

Rainbow trout (*Oncorhyncus mykiss*), all female stock with an initial body weight of approximately 27.3 g, were fed a practical basal diet containing 49% SBM (Soy Bean Meal) and 12% FM (Fish Meal), without (Control), and with, addition of the protease of the invention having amino acids 1–188 of SEQ ID NO: 2, in an amount of 50 mg protease enzyme protein/kg feed. Fish were fed ad libitum. The feeding trial was performed in 500 l tanks, part of a semi-recirculating unit with a water temperature of 15° C.+/−1° C., with 50 fish per tank and 4 replicates per treatment. Survival, growth, and feed conversion were measured over an 85-days feeding period.

The results are shown in Table 15 below. A significant increase in bodyweight was obtained by addition of the protease of the invention to the diet.

TABLE 15

| | In vivo fish results | | | |
|---|---|---|---|---|
| Treatment | Survival % | Initial Body Weight/g | Final Body Weight/g | Weight Gain/g |
| Control | 100.0 +/− 0.0 | 27.3 +/− 0.0 | 305.0 +/− 5.3 | 277.7 +/− 5.3 |
| Protease 1–188 of SEQ ID NO: 2 | 100.0 +/− 0.0 | 27.3 +/− 0.0 | 333.5 +/− 4.7 | 306.2 +/− 4.7 |

Example 12

Proteolytic Degradation of Major Purified Soybean Proteins

We have studied the ability of the protease from *Nocardiopsis* sp. NRRL 18262 and the protease of the invention having amino acids 1–188 of SEQ ID NO: 2 to degrade purified soy proteins. The purified soy proteins studied were three so-called anti-nutritional factors of soy protein: Soybean agglutinin (SBA), the soybean Kunitz trypsin inhibitor, the soybean Bowman-Birk inhibitor; and two of the major storage proteins from soy: Glycinin and beta-conglycinin.

These soy proteins were obtained as follows: SBA was purified from unheated soybean meal (prod. No. S-9633, Sigma) by affinity chromatography using N-aminocaproyl-beta-D-galactopyranosylamine Sepharose (Sigma) Fractions eluting from the column were analysed using SDS-PAGE (Tris-glycine 4–20%), and fractions containing essentially pure protein were pooled. Soybean glycinin and beta-conglycinin were purified according to the procedures described by Fischer, M. et al: Enzymatic Extractability of Soybean Meal Proteins and Carbohydrates: Heat and Humidity Effects. J. Agric. Food Chem. 2001, 49, 4463–4469. The Bowman-Birk inhibitor and the Kunitz trypsin inhibitor are commercial products (Sigma T-9777 and Fluka 93618, respectively).

The purified soy proteins were incubated with the two proteases for 4 hours at 37° C. and pH 6.5 (protease: soy protein=1:10, based on $A_{280}$). Incubation buffer: 50 mM dimethyl glutaric acid, 150 mM NaCl, 1 mM $CaCl_2$, 0,01% Triton X-100, pH 6.5.

The ability of the proteases to degrade each of these five proteins was estimated as the relative intensity decrease of the intact soy protein band on SDS-PAGE (Tris-glycine 4–20%) gels stained with Coomassie Brilliant Blue. In case of glycinin and beta-conglycinin, the term "the intact soy protein band" in fact refers to two and three bands, respectively, as these two proteins, when subjected to the reducing environment on the SDS-PAGE gel, denature under the formation of two and three sub-units, respectively.

The intensity of the intact soy protein bands (before and after treatment with the two proteases) was determined by scanning the stained SDS gels, and the degradation of each of the five proteins by each of the two proteases determined as the intensity of the respective intact soy protein band after, relative to the intensity of the respective intact soy protein band before the protease treatment. The percentage protein degradation is calculated as follows: 100%−((band intensity after/band intensity before)×100%). The results are shown in Table 16 below.

TABLE 16

Percentage degradation of isolated soy proteins

| Protease | SBA | Bowman-Birk Inhibitor | Kunitz trypsin Inhibitor | Glycinin | Beta-conglycinin |
|---|---|---|---|---|---|
| From *Nocardiopsis* sp. NRRL 18262 | 100 | 35 | 94 | 98 | 95 |
| Protease having amino acids 1–188 of SEQ ID NO: 2 | 95 | 81 | 97 | 100 | 100 |

Example 13

Animal Feed and Animal Feed Additives

An animal feed additive comprising the protease of the invention having amino acids 1–188 of SEQ ID NO: 2, in the form of a vitamins and mineral premix, is composed as shown in Table 17 below. The vitamins and the carotenoids are commercially available from DSM Nutritional Products. All amounts are in g/kg.

TABLE 17

| | Premix composition | |
|---|---|---|
| Vitamin A | ROVIMIX A 500 | 4.00 |
| Vitamin D3 | ROVIMIX D3 500 | 1.00 |
| Vitamin E | ROVIMIX E 50 Ads | 8.00 |
| Vitamin B2 | ROVIMIX B2 80-SD | 1.0 |
| | CAROPHYLL Yellow | 10.0 |
| | Choline chloride 50%, min. | 300.0 |
| Minerals | Mn Oxide | 60.0 |
| | Zn Oxide | 12.0 |
| | Fe Sulphate monohydrate | 20.0 |
| | Cu Oxide | 2.0 |
| | Co Sulphate | 0.2 |
| Enzyme | Protease having amino acids 1–188 of SEQ ID NO: 2 (enzyme protein) | 3.0 |
| | Wheat middlings | 578.8 |

The Premix of Table 17 is included in a trout feed with a composition as shown in Table 18 below. The amount of each ingredient is indicated in % (w/w). The in-feed-concentration of the protease of the invention is 51 mg protease enzyme protein per kg.

TABLE 18

| Trout feed composition | |
|---|---|
| Wheat | 11.20 |
| Soya | 14.00 |
| Fish meal | 57.00 |
| Soya oil | 4.00 |
| Starch | 8.00 |
| Yeast | 4.00 |
| Choline chloride 75% | 0.10 |
| Premix of Table 17 | 1.70 |

We claim:

1. An isolated polypeptide having protease activity, and having a melting temperature ($T_m$) of at least 78° C., as determined by Differential Scanning Calorimetry (DSC) in a 10 mM sodium phosphate, 50 mM sodium chloride buffer, pH 7.0, using a constant scan rate of 1.5° C./min, wherein the polypeptide is selected from the group consisting of:
   (a) a polypeptide having an amino acid sequence which has a degree of identity to amino acids 1 to 188 of SEQ ID NO: 2 of at least 90%, wherein % identity is determined by the Clustal method;
   (b) a polypeptide which is encoded by a nucleic acid sequence which hybridizes under high stringency conditions with nucleotides 499–1062 of SEQ ID NO: 1; and
   (c) a polypeptide which is encoded by a nucleic acid sequence which has a degree of identity to nucleotides 499–1062 of SEQ ID NO: 1 of at least 90%.

2. The polypeptide of claim 1, which has an amino acid sequence which has a degree of identity to amino acids 1 to 188 of SEQ ID NO: 2 of at least 90%.

3. The polypeptide of claim 1, which has an amino acid sequence which has a degree of identity to amino acids 1 to 188 of SEQ ID NO: 2 of at least 92%.

4. The polypeptide of claim 1, which has an amino acid sequence which has a degree of identity to amino acids 1 to 188 of SEQ ID NO: 2 of at least 94%.

5. The polypeptide of claim 1, which has an amino acid sequence which has a degree or identity to amino acids 1 to 188 of SEQ ID NO: 2 of at least 96%.

6. The polypeptide of claim 1, which has an amino acid sequence which has a degree of identity to amino acids 1 to 188 of SEQ ID NO: 2 of at least 98%.

7. The polypeptide of claim 1, which has an amino acid sequence which has a degree of identity to amino acids 1 to 188 of SEQ ID NO: 2 of at least 99%.

8. The polypeptide of claim 1, which has an amino acid sequence which has a sequence of amino acids 1 to 188 of SEQ ID NO: 2 or a fragment thereof, wherein the fragment has protease activity.

9. The polypeptide of claim 1, which has the following amino acids at the indicated positions 10Y, 24S, 38T, 42G, 49T, 51T, 53Q, 54N, 82S, 86Q, 87S, 89T, 91T, 92S, 96A, 99A, 118N, 120T, 122R, 125Q, 129Y, 130S, 131L, 135N, 147F, 151S, 165S, 166V, 171Y, 179I, and/or 186I.

10. The polypeptide of claim 1, which is encoded by a nucleic acid sequence which hybridizes under high stringency conditions with nucleotides 499–1062 of SEQ ID NO: 1.

11. The polypeptide of claim 1, which is encoded by a nucleic acid sequence which hybridizes under very high stringency conditions with nucleotides 499–1062 of SEQ ID NO: 1.

12. The polypeptide of claim 1, which is encoded by a nucleic acid sequence which has a degree of identity to nucleotides 499–1062 of SEQ ID NO: 1 of at least 90%.

13. An animal feed additive comprising the polypeptide of claim 1 and one or more of:
 (a) at least one tat-soluble vitamin,
 (b) at least one water-soluble vitamin, and
 (c) at least one trace mineral.

14. An animal feed composition having a crude protein content of 50 to 800 g/kg and comprising the polypeptide of claim 1.

15. An animal feed composition having a crude protein content of 50 to 800 gl/kg and comprising the feed additive of claim 13.

16. The animal feed composition of claim 14 which is a fish feed.

17. A composition comprising the polypeptide of claim 1, and at least one other enzyme selected from the group consisting of amylase, phytase, xylanase, galactanase, alpha-galactosidase, protease, phospholipase, and beta-glucanase.

18. A detergent composition comprising the polypeptide of claim 1 and a surfactant.

19. A method for improving the nutritional value of an animal feed, comprising adding the polypeptide of claim 1 to the animal feed.

20. A method for increasing digestible and/or soluble protein in an animal diet and/or for increasing the degree of hydrolysis of proteins in an animal diet, comprising adding the polypeptide of claim 1 to the animal diet.

* * * * *